United States Patent
Niles

(10) Patent No.: US 8,227,205 B2
(45) Date of Patent: Jul. 24, 2012

(54) LUMINESCENT LIVE AND DEAD CELL ASSAY

(75) Inventor: Andrew Niles, Madison, WI (US)

(73) Assignee: Promega Corporation, Madison, WI (US)

( * ) Notice: Subject to any disclaimer, the term of this patent is extended or adjusted under 35 U.S.C. 154(b) by 1103 days.

(21) Appl. No.: 12/100,889

(22) Filed: Apr. 10, 2008

(65) Prior Publication Data

US 2012/0149045 A1 Jun. 14, 2012

Related U.S. Application Data

(60) Provisional application No. 60/923,376, filed on Apr. 13, 2007.

(51) Int. Cl.
*C12Q 1/66* (2006.01)
*C12Q 1/37* (2006.01)
*C12Q 1/02* (2006.01)

(52) U.S. Cl. .................. 435/8; 435/23; 435/29

(58) Field of Classification Search ............. None
See application file for complete search history.

(56) References Cited

U.S. PATENT DOCUMENTS

| | | |
|---|---|---|
| 4,557,862 A | 12/1985 | Mangel et al. |
| 4,640,893 A | 2/1987 | Mangel et al. |
| 4,908,309 A | 3/1990 | Cho et al. |
| 5,035,999 A | 7/1991 | Geiger et al. |
| 5,098,828 A | 3/1992 | Geiger et al. |
| 5,314,805 A | 5/1994 | Haugland et al. |
| 5,698,411 A | 12/1997 | Lucas et al. |
| 5,744,320 A | 4/1998 | Sherf et al. |
| 5,834,196 A | 11/1998 | Reutelingsperger |
| 5,976,822 A | 11/1999 | Landrum et al. |
| 6,251,614 B1 | 6/2001 | Fritz et al. |
| 6,270,980 B1 | 8/2001 | Fritz et al. |
| 6,335,429 B1 | 1/2002 | Cai et al. |
| 6,586,196 B1 | 7/2003 | Bronstein et al. |
| 6,602,657 B1 | 8/2003 | Bronstein et al. |
| 6,613,541 B1 | 9/2003 | Vaddi et al. |
| 6,759,207 B2 | 7/2004 | Weber et al. |
| 6,811,990 B1 | 11/2004 | Corey et al. |
| 6,890,745 B1 | 5/2005 | Leng |
| 7,148,030 B2 | 12/2006 | O'Brien et al. |
| 7,384,758 B2 | 6/2008 | O'Brien et al. |
| 7,416,854 B2 | 8/2008 | Riss et al. |
| 2002/0068316 A1 | 6/2002 | Rust et al. |
| 2002/0119500 A1 | 8/2002 | Xue et al. |
| 2003/0211560 A1 | 11/2003 | O'Brien et al. |
| 2004/0171099 A1 | 9/2004 | Cali et al. |

(Continued)

FOREIGN PATENT DOCUMENTS

AU 199878177 12/1998

(Continued)

OTHER PUBLICATIONS

European Patent Office Action for Application No. 06790059.7 dated Nov. 26, 2009 (4 pages).

(Continued)

*Primary Examiner* — Chris R Tate
*Assistant Examiner* — Douglas F White
(74) *Attorney, Agent, or Firm* — Michael Best & Friedrich LLP

(57) ABSTRACT

A method to detect live and dead cells in a sample with one bioluminogenic reagent is provided.

20 Claims, 14 Drawing Sheets

U.S. PATENT DOCUMENTS

| | | |
|---|---|---|
| 2005/0164321 A1 | 7/2005 | Riss et al. |
| 2006/0121546 A1 | 6/2006 | O'Brien et al. |
| 2006/0183177 A1 | 8/2006 | O'Brien et al. |
| 2007/0178545 A1 | 8/2007 | Niles et al. |
| 2008/0268482 A1 | 10/2008 | Riss et al. |
| 2009/0017482 A1 | 1/2009 | Riss et al. |
| 2009/0275051 A1 | 11/2009 | Niles et al. |
| 2010/0249427 A1 | 9/2010 | O'Brien et al. |

FOREIGN PATENT DOCUMENTS

| | | |
|---|---|---|
| EP | 1382691 A2 | 1/2004 |
| JP | 63501571 | 6/1988 |
| JP | 01-502431 | 8/1989 |
| JP | 2001519368 | 4/1999 |
| JP | 11341998 | 12/1999 |
| JP | 2000513563 | 10/2000 |
| WO | WO-88/05434 A1 | 7/1988 |
| WO | WO-00/36098 A1 | 6/2000 |
| WO | WO-00/50630 A2 | 8/2000 |
| WO | WO-00/52194 A2 | 9/2000 |
| WO | WO-01/46694 A2 | 6/2001 |
| WO | WO-01/57242 A2 | 8/2001 |
| WO | WO-02/00882 A2 | 1/2002 |
| WO | WO-02/006458 A2 | 1/2002 |
| WO | WO-02/12547 A1 | 2/2002 |
| WO | WO-03/025192 A2 | 3/2003 |
| WO | WO-03/066611 A1 | 8/2003 |
| WO | WO-2005/073722 A2 | 8/2005 |
| WO | WO-2007/027653 A1 | 3/2007 |
| WO | WO-2008/127677 A2 | 10/2008 |
| WO | WO2005073722 * | 8/2011 |

OTHER PUBLICATIONS

United States Patent Office Notice of Allowance for U.S. Appl. No. 12/706,078 dated Jul. 25, 2011 (2 pages).

United States Patent Office Action for U.S. Appl. No. 12/146,245 dated Jul. 6, 2011 (8 pages).

European Patent Office Action for Application No. 03737580.5 dated Jun. 8, 2010 (8 pages).

Boonacker, E. et al., "Fluorogenic substrate [ala-pro]2-cresyl violet but not ala-pro-rhodamine 110 is cleaved specifically by DPPIV activity: a study in living jurkat cells and CD26/DPPIV-transfected jurkat cells," J. Histo. Cytochem. (2003) 51(7):959-968.

Ganesh, S. et al., "Flow cytometric determination of aminopeptidase activities in viable cells using fluorogenic rhodamine 110 substrates," Cytometry (1995) 20:334-340.

United States Patent Office Action for U.S. Appl. No. 12/494,100 dated Sep. 15, 2011 (14 pages).

Hiraoka, Y. et al., "Rapid assessment of the physiological status of the polychlorinated biphenyl degrader comamonas testosteroni TK102 by flow cytometry," Appl. Environ. Microbiol. (2002) 2031-2035.

Japanese Patent Office Action for Application No. 2006-551360 dated Sep. 28, 2010 (11 pages) English translation only.

Canadian Patent Office Action for Application No. 2,474,695 dated Mar. 10, 2010 (3 pages).

European Patent Office Action for Application No. 08742813.2 dated Mar. 10, 2010 (2 pages).

"Apo-ONE@ Homogeneous Caspase-3/7 Assay", *Promega Online Catalog*, [online]. [retrieved Jun. 2, 2003]. Retrieved from the Internet: <URL: www.promega.com>, (2006), 2 pgs.

"Apo-ONE™ Homogeneous Caspase-3/7 Assay", *Promega Technical Bulletin No. 295*, (Part# TB295), (May, 2001), 12 pgs.

"Apoptosis Inducers and the Assay of Caspase Activity Biomol", *Fased Journal*, 2(8), Abstract No. T10, Federation of American Studies for Experimental Biology, (Apr. 24, 1998), p. A1488.

"Apoptosis: Annexin V & Propidium Iodide—Freedom to Discover", *Acumen Bioscience Ltd.*, (Prior to Jan. 20, 2004), 2 pgs.

"U.S. Appl. No. 10/356,665, Response filed Nov. 10, 2005 to Non-Final Office Action mailed Aug. 12, 2005", 18 pgs.

"U.S. Appl. No. 10/356,665, Non Final Office Action mailed Aug. 12, 2005", 7 pgs.

"U.S. Appl. No. 10/356,665, Notice of Allowance mailed Jan. 25, 2906", 7 pgs.

"U.S. Appl. No. 10/356,665, Restriction Requirement mailed Jun. 7, 2003", 7 pgs.

"U.S. Appl. No. 10/356,665, Supplemental Preliminary Amendment and Response filed Jun. 29, 2005 to Restriction Requirement mailed Jun. 7, 2003", 14 pgs.

"U.S. Appl. No. 11/347,054, Response filed Jun. 24, 2008 to Final Office Action mailed Jan. 10, 2008", 7 pgs.

"U.S. Appl. No. 11/347,054, Final Office Action mailed Jan. 10, 2008", 7 pgs.

"U.S. Appl. No. 11/347,054, Amendment and Response filed Nov. 27, 2007 to Office Action mailed Sep. 11, 2007", 13 pgs.

"U.S. Appl. No. 11/347,054, Non-Final Office Action mailed Sep. 11, 2007", 7 pgs.

"U.S. Appl. No. 11/347,054, Response filed Jan. 28, 2009 to Non-Final Office Action mailed Jul. 28, 2008", 12 pgs.

"U.S. Appl. No. 11/347,054, Non-Final Office Action mailed Jul. 28, 2008", 7 pgs.

"U.S. Appl. No. 11/347,054, Final Office Action mailed on Mar. 6, 2009", 8 pgs.

U.S. Appl. No. 11/347,054, Response filed Aug. 6, 2007 to Restriction Requirement mailed Jul. 6, 2007, 11 pgs.

"U.S. Appl. No. 11/347,054, Restriction Requirement mailed Jul. 6, 2007", 7 pgs.

"U.S. Appl. No. 11/347,054, Preliminary Amendment filed Feb. 3, 2006", 9 pgs.

"U.S. Appl. No. 10/762,836,Response filed Nov. 2, 2006 Non-Final Office Action mailed Sep. 8, 2006", 15 pgs.

"U.S. Appl. No. 10/762,836, RCE/Preliminary Amendment filed Aug. 31, 2007", 6 pgs.

"U.S. Appl. No. 10/762,836, Notice of Allowance mailed Mar. 25, 2008", 7 pgs.

"U.S. Appl. No. 10/762,836, Notice of Allowance mailed Nov. 7, 2007", 8 pgs.

"U.S. Appl. No. 10/762,836, Final Office Action mailed Feb. 2, 2007", 8 pgs.

"U.S. Appl. No. 10/762,836, Non-Final Office Action mailed Mar. 21, 2006", 16 pgs.

"U.S. Appl. No. 10/762,836, Non-Final Office Action mailed Sep. 8, 2006", 8 pgs.

"U.S. Appl. No. 10/762,836, Notice of Allowance mailed May 31, 2007", 6 pgs.

"U.S. Appl. No. 10/762,836, Response filed Apr. 2, 2007 to Final Office Action mailed—Feb. 2, 2007", 24 pgs.

"U.S. Appl. No. 10/762,836, Response filed Jun. 21, 2006 Non-Final Office Action mailed Mar. 21, 2006", 23 pgs.

"U.S. Appl. No. 11/346,043, Amendment and Response filed Dec. 17, 2007 to Office Action mailed Nov. 5, 2007", 11 pgs.

"U.S. Appl. No. 11/346,043, Amendment filed Apr. 28, 2008 to Notice of Allowance mailed Jan. 28, 2008", 3 pgs.

"U.S. Appl. No. 11/346,043, Non-Final Office Action mailed Nov. 5, 2007", 8 pgs.

"U.S. Appl. No. 11/346,043, Notice of Allowance mailed Jan. 28, 2008", 6 pgs.

"U.S. Appl. No. 11/346,043, Response filed Aug. 6, 2007 to Restriction Requirement mailed Jul. 6, 2007", 7 pgs.

"U.S. Appl. No. 11/346,043, Response filed Oct. 1, 2007 to Restriction Requirement mailed Aug. 31, 2007", 7 pgs.

"U.S. Appl. No. 11/346,043, Response to Rule 312 Communication filed May 1, 2008", 2 pgs.

"U.S. Appl. No. 11/346,043, Restriction Requirement mailed Jul. 6, 2007", 4 pgs.

"U.S. Appl. No. 11/346,043, Restriction Requirement mailed Aug. 31, 2007", 4 pgs.

"U.S. Appl. No. 11/489,978, Non-Final Office Action mailed Feb. 1, 2008", 13 pgs.

"U.S. Appl. No. 11/489,978, Response filed Apr. 23, 2008 to Non-Final Office Action mailed Feb. 1, 2008", 21 pgs.

"U.S. Appl. No. 11/489,978, Restriction Requirement mailed Nov. 28, 2008", 9 pgs.

"U.S. Appl. No. 11/489,978, Notice of Allowance mailed Feb. 26, 2009", 8 pgs.

"U.S. Appl. No. 11/489,978, Notice of Allowance mailed Jul. 28, 2008", 12 pgs.

"U.S. Appl. No. 11/489,978, Response filed Dec. 21, 2007 to Restriction Requirement mailed Nov. 28, 2007", 7 pgs.
"U.S. Appl. No. 11/510,278, Non-Final Office Action mailed May 30, 2008", 13 pgs.
"U.S. Appl. No. 11/510,278, Restriction Requirement mailed Jan. 31, 2008", 8 pgs.
"U.S. Appl. No. 11/510,278, Response filed Nov. 26, 2008 to Non-Final Office Action mailed May 30, 2008", 18 pgs.
"U.S. Appl. No. 11/510,278, Response to Restriction Requirement and Preliminary Amendment filed Mar. 3, 2008 in Response to Restriction Requirement mailed Jan. 31, 2008.", 8 pgs.
"U.S. Appl. No. 11/510,278, Non-Final Office Action mailed Jan. 22, 2009", 21 pgs.
"U.S. Appl. No. 11/510,278, Response filed May 22, 2009 to Non-Final Office Action mailed Jan. 22, 2009", 14 pgs.
"U.S. Appl. No. 11/897,743, Non-Final Office Action mailed May 29, 2009", 15 pgs.
"Australian Application Serial No. 2003216139, Examiner's First Report mailed Mar. 5, 2008", 4 pgs.
"Australian Application Serial No. 2003216139, Notice of Acceptance mailed Aug. 1, 2008", 11 pgs.
"Australian Application Serial No. 2003216139, Response filed Jul. 30, 2008 to Examiner's First Report mailed Mar. 5, 2008", 28 pgs.
"Beadlyte® Multiplex Assay Systems", *Product Guide, Upstate Cell Signalling Solutions*, (2002), 12 pgs.
"Canadian Application Serial No. 2,474,695, Voluntary Amendment mailed Jan. 25, 2008", 12 pgs.
"Caspase-Glo ™ 3/7 Assay", *Technical Bulletin No. 323, Promega Corporation*, (May 2003), 13 pgs.
"Cell Cytotoxicity—Freedom to Discover", *Acumen Bioscience Ltd.*, (Prior to Jan. 20, 2004), 2 pgs.
"Cell Proliferation—Freedom to Discover", *Acumen Bioscience Ltd.*, (Prior to Jan. 22, 2002), 2 pgs.
"CellTiter-Blue™ Cell Viability Assay", *Technical Bulletin No. 317, Promega Corporation*, (Dec. 2002), 12 pgs.
"CellTiter-Glo™ Luminescent Cell Viability Assay", *Technical Bullentin No. 288, Promega Corporation*, (May, 2001), 11 pgs.
"CleavaLite™: New Bioluminescent Caspase-3 Activity Assay", *Chemicon International Communications Update*, vol. 11, No. 2, (published before May 16, 2001), 1 pg.
"CytoTox-ONE™ Homogeneous Membrane Integrity Assay", *Technical Bulletin No. 306, Promega Corporation*, (May, 2003), 13 pgs.
"Dual-Light ® Luminescent Report Gene Assay for Luciferase and Beta-Galactosidase", *Data Sheet, Applied Biosystems*, (2000), 2 pgs.
"European Application Serial No. 03737580.5, Communication mailed Jan. 16, 2007", 3 pgs.
"European Application Serial No. 03737580.5, Response filed Jul. 26, 2007 to Communication mailed Jan. 16, 2007", 8 pgs.
"European Application Serial No. 06790059.7, Communication mailed Sep. 23, 2008", 2 pgs.
"European Application Serial No. 06790059.7, Response filed Mar. 20, 2009 to Communication mailed Sep. 23, 2008", 26 pgs.
"European Application Serial No. 06790059.7, Communication mailed Apr. 16, 2009", 5 pgs.
"International Application No. PCT/US2005/002158, Partial International Search Report mailed Oct. 12, 2006", 2 pgs.
"International Application Serial No. PCT/US03/02936, Amendment filed Feb. 3, 2004 to Written Opinion mailed Nov. 12, 2003", 16 pgs.
"International Application Serial No. PCT/US03/02936, International Preliminary Examination Report mailed Apr. 26, 2004", 18 pgs.
"International Application Serial No. PCT/US03/02936, International Search Report mailed Jul. 7, 2003", 4 pgs.
"International Application Serial No. PCT/US03/02936, Written Opinion mailed Sep. 24, 2003", 2 pgs.
"International Application Serial No. PCT/US03/02936, Written Opinion mailed Nov. 12, 2003", 6 pgs.
"International Application Serial No. PCT/US2005/002158, International Search Report mailed Jun. 14, 2007", 8 pgs.
"International Application Serial No. PCT/US2005/002158, Written Opinion mailed Jun. 14, 2007", 9 pgs.
"International Application Serial No. PCT/US2006/033622, International Search Report mailed Dec. 28, 2006", 6 pgs.
"International Application Serial No. PCT/US2006/033622, Written Opinion mailed Dec. 28, 2006", 7 pgs.
"International Application Serial No. PCT/US2008/004748, International Search Report mailed Nov. 7, 2008", 5 pgs.
"International Application Serial No. PCT/US2008/004748, Written Opinion mailed Nov. 7, 2008", 7 pgs.
"Japanese Application Serial No. 2003-565985, Argument and Amendment filed Nov. 28, 2008 to Official Action mailed—Jul. 1, 2008", 10 pgs.
"Japanese Application Serial No. 2003-565985, Official Action mailed—Jul. 1, 2008", (English Translation), 4 pgs.
"Japanese Application Serial No. 2003-565985, Office Action mailed Feb. 6, 2009", (w/ English Translation), 7 pgs.
"Multiplex Antibody Kits Custom Software & Hardware for Luminex tm", *MiraiBio Inc.*, (Prior to Jan. 20, 2004), 2 pgs.
"New Products—ApoAlert™CPP32 Protease Assay Kits", *CLONTECHniques*, (Jan. 1997), 4-6.
"UniCAP® Tryptase", [online}. [retrieved Jan. 24, 2002]. Retrieved from the Internet: <URL: http://www.labspec.co.za/tryptase.html>, (Jan. 2002), 6 pgs.
Adrain, C., et al., "Apoptosis-Associated Release of Smac/DIABLO From Mitochondria Requires Active Caspases and is Blocked by Bcl-2", *The EMBO Journal*, 20(23), (2001), 6627-6636.
Armstrong, R. C., et al., "Activation of the CED3/ICE-Related Protease CPP32 in Cerebellar Granule Neurons Undergoing Apoptosis but Not Necrosis", *The Journal of Neuroscience*, 17(2), (Jan. 15, 1997), 553-562.
Batchlor, R. H, et al., "Use of cellular glucose-6-phosphate dehydrogenase for cell quantitation: applications in cytotoxicity and apoptosis assays", *Analytical Biochemistry*, 329(1), (2004), 35-42.
Berkers, C. R., et al., "Activity Probe for in vivo Profiling of the Specificity of Proteasome Inhibitor Bortezomib", *Nature Methods*, 2(5), (2005), 357-362.
Bond, J. S., et al., "Intracellular Proteases", *Annual Review of Biochemistry*, 56, (1987), 333-364.
Bronstein, I., et al., "Combined Luminescent Assays for Multiple Enzymes", *Bioluminescence and Chemiluminescence: Molecular Reporting With Photons*, (International Symposium Proceedings), (1997), 451-457.
Chang H. Y., et al., "Proteases for Cell Suicide: Functions and Regulation of Caspases", *Microbiology and Molecular Biology Reviews: MMBR. United States*, 46, (2000), 821-846.
Constam, D. B., et al., "Purumycin-Sensitive Aminopeptidase", *The Journal of Biological Chemistry*, 270(45), (1995), 26931-26939.
Cook, J. A., et al., "Viability Measurements in Mammalian Cell Systems", *Analytical Biochemistry*, 179, (1989), 1-7.
Corey, M. J., et al., "A very sensitive coupled luminescent assay for cytotoxicity and complement-mediated lysis", *Journal of Immunological Methods*, 207, (1997), 43-51.
Damour, M., et al., "Non-Radioactive Multiplex Kinase Activity Assay Using Beadlyte (r) Suspension Microarrays", (Prior to Jan. 20, 2004), 1 pg.
De Jager, W., et al., "Simultaneous Detection of 15 Human Cytokines in a Single Sample of Stimulated Peripheral Blood Mononuclear Cells", *Clinical and Diagnostic Laboratory Immunology*, 10(1), (2003), 133-139
Dyer, B., et al., "A Noncommercial Dual Luciferase Enzyme Assay System for Report Gene Analysis", *Analytical Biochemistry*, 282, (2000), 158-161.
Farfan, A., et al., "Frequently Asked Questions Cytotox-One™ tm Homogeneous Membrane Integrity Assay", *Cell Notes, Issue 6*, (2003), 19-20.
Fenteany, G, et al., "Inhibition of proteasome activities and subunit-specific amino-terminal threonine modification by lactacystin", *Science*, 268(5211), (1995), 726-731.
Fernandes-Alnemri, T., et al., "In vitro activation of CPP32 and Mch3 by Mch4, a novel human apoptotic cysteine protease containing two FADD-like domains", *Proceedings of National Academy of Science USA*, 93(15), (Jul. 1996) 7464-7469.

Fernandez, Y., et al., "Differential Regulation of Noxa in Normal Melanocytes and Melanoma Cells by Proteasome Inhibition: Therapeutic Implications", *Cancer Research*, 65(14), (2005), 6294-6304.

Garcia-Calvo, M, et al., "Purification and catalytic properties of human caspase family members.", *Cell Death & Differentiation.* 6(41, (1999), 362-369.

Golabek, A. A., et al., "Biosynthesis, Glycosylation, and Enzymatic Processing in Vivo of Human Tripeptidyl-peptidase I", *Journal of Biological Chemistry*, 278(9), (2003), 7135-7145.

Grant, S. K., et al., "Development of Novel Assays for Proteolytic Enzymes Using Rhodamine-Based Fluorogenic Substrates", *Journal of Biomolecular Screening*, 7(6),(2002), 531-540.

Gurtu, V., et al., "Fluorometric and Colorimetric Detection of Caspase Activity Associated with Apoptosis", *Analytical Biochemistry*, 251, (1997), 98-102.

Haunstetter, A., et al., "Apoptosis: Basic Mechanisms and Implications for Cardiovascular Disease", *Circulation Research*, 82, (1998), 1111-1129.

Karlsson, J. O, et al., "Proteolytic Activity in Intact Sheets of Polarized Epithelial Cells as Determined by a Cell-Permeable Fluorogenic Substrate", *Cell Biology International*,24(4), (2000), 235-243.

Kisselev, A. F., et al., "The Caspase-Like Sites of Proteasomes,Their Substrate Specificity,New Inhibitors and Substrates,and Allosteric Interactions with the Trypsin-Like Sites", *The Journal of Biological Chemistry*, 278 (38), (2003), 35869-35877.

Kisselev, A. F., et al., "Binding of Hydrophobic Peptides to Several Non-catalytic Sites Promotes Peptide Hydrolysis by All Active Sites of 20 S Proteasomes", *Journal of Biological Chemistry*, 277(25), (2002), 22260-22270.

Kisselev, A. F., et al., "Importance of the Different Proteolytic Sites of the Proteasome and the Efficacy of Inhibitors Varies With Protein Substrate", *The Journal of Biological Chemistry*, 281(13), (Mar. 31, 2006), 8582-8590.

Kisselev, A. F., et al., "Monitoring Activity and Inhibition of 26S Proteasomes With Fluorogenic Peptide Substrates", *Methods in Enzymology*, vol. 398, (2005), 364-378.

Liu, J., et al., "Visualizing and Quantifying Protein Secretion Using A Renialla luciferase-GFP Fusion Protein", *Luciferase*, 15(1), (Feb. 2000), 45-49.

Los, M., et al., "Requirement of an ICE/CED-3 Protease for Fas/APO-1-Mediated Apoptosis", *Nature*, 375, (May 4, 1995), 91-93.

Luker, G. D., et al., "Imaging 26S Proteasome Activity and Inhibition in Living Mice", *Nature Medicine*, 9(7), (2003), 969-973.

Mandlekar, S., et al., "Activation of Caspase-3 and c-Jun $NH_2$-terminal Kinase-1 Signaling Pathways in Tamoxifen-induced Apoptosis of Human Breast Cancer Cells", *Cancer Research*, 60, (2000), 5995-6000.

Martin, C. S., "Dual Luminescence-Based Reporter Gene Assay for Luciferase and β-Galactosidase", *BioTechniques*, 21(3), (1996), 520-524.

Masuda-Nishimura, I., et al., "Development of a rapid positive/absent test for coliforms using sensitive bioluminescence assay", *Letters in Applied Microbiology*, 30, (2000), 130-135.

Mellgren, R. L., et al., "Specificities of Cell Permeant Peptidyl Inhibitors for the Proteinase Activities of μ-Calpain and the 20 S Proteasome", *The Journal of Biological Chemistry*, 272(47), (1997), 29899-29903.

Merrifield, B., "Solid Phase Synthesis", *Science*, 232, (1986), 341-347.

Miska, W., et al., "A New Type of Ultrasensitive Bioluminogenic Enzyme Subsrates", *Biol. Chem. Hoppe-Seyler*, (May, 1988), 407-411.

Miska, Werner, et al., "Synthesis and Characterization of Luciferin Derivatives for Use in Bioluminescence Enhanced Enzyme Immunoassays", *Journal of Clinical Chemistry and Clinical Biochemistry*, 25, (1987), 23-30.

Monsees, T., et al., "A Novel Bioluminogenic Assay for a-Chymotrypsin", *Journal of Bioluminescence and Chemiluminescence*, 10(4), (1995), 213-218.

Monsees, T., et al., "Synthesis and Characterization of a bioluminogenic substrate for α-chymotrypsin", *Analytical Biochemistry*; 221(2), (1994), 329-334.

Myers, M. A., "Direct Measurement of Cell Numbers in Microtitre Plate Cultures Using the Fluorescent Dye SYBR Green", *Journal of Immunological Methods*, 212, (1998), 99-103.

Nicholson, D. W, et al., "Identification and inhibition of the ICE/CED-3 protease necessary for mammalian apoptosis", *Nature*, 376, (Jul. 1995), 37-43.

Niles, A. L, et al., "A homogeneous assay to measure live and dead cells in the same sample by detecting different protease markers", *Analytical Biochemistry*, 366(2), (2007), 197-206.

Nolkrantz, Kerstin, et al., "Functional Screening of Intracellular Proteins in Single Cells and in Patterned Cell Arrays Using Electroporation", *Analytical Chemistry*, 74(16),(2002), 4300-4305.

O'Brien, M. A, et al., "Homogeneous Bioluminescent Protease Assays : Caspase-3 as a Model", *Journal of Biomolecular Screening*,10(2), (2005), 137-148.

O'Connell, et al., "Live/Dead Assay for Cell Viability; AfCS Procedure Protocol PP00000023", http://wwwsignaling-gateway.org/data/cgi-bin/ProtocolFile.cgi/afcs_PP00000023.pdf?pid=PP00000023, (2002), 1-5 pgs.

Ogbomo, H., et al., "NK sensitivity of neuroblastoma cells determined by a highly sensitive coupled luminescent method", *Biochemical and Biophysical Research Communications*, 339(1), (/2006), 375-379.

Preta, G., et al., "Inhibition of Serine-Peptidase Activity Enhances the Generation of a Survivin-Derived HLA-A2-Presented CTL Epitope in Colon-Carcinoma Cells", *Scand J Immunol.*, 68(6), (Dec. 2008), 579-88.

Princiotta, et al., "Cells Adapted to the Proteasome Inhibitor 4-Hydroxy-5-Iodo-3-Nitrophenylacetyl-Leu-Leu-Leucinal-Vinyl Sulfone Require Enzymatically Active Proteasome for Continued Survival", *Proceeding of the National Academy of Sciences*, vol. 98(2), (2001), 513-519.

Qazi, Saara, et al., "A Novel Dual Reporter Assay for Studying Intracellular Bacterial Pathogens", *Luminescence*, 17, (Abstract Only), XIIth International Symposium on Bioluminescence and Chemiluminescence, (2002), p. 106.

Ramsby, M. L., "Differential Detergent Fractionation of Isolated Hepatocyes: Biochemical, Immunochemical and Two-Dimensional Gel Electrophoresis Characterization of Cytoskeletal and Noncytoskeletal Compartments", *Electrophoresis*, 15, (1994), 265-277.

Ranjit, G. B., et al., "Poly(adenosine diphosphoribose) Polymerase in Peripheral Blood Leukocytes From Normal Donors and Patients With Malignancies", *Clinical Cancer Research*, 1(2), (1995), 223-234.

Riss, T. L., et al., "Use of Multiple Assay Endpoints to Investigate the Effects of Incubation Time, Dose of Toxin, and Plating Density in Cell-Based Cytotoxicity Assasys", *Assay and Drug Development Technologies*, 2(1), (Abstract Only), (2004), 1 pg.

Rosser, et al., "Calpain activity increases in hepatocytes following addition of ATP", *The Journal of Biological Chemistry*, vol. 268, No. 31, (1993), 23593-23600.

Schulz, Jorg B., et al., "Potassium Deprivation-Induced Apoptosis of Cerebellar Granule Neurons: A Sequential-Requirement for New mRNA and Protein Synthesis, ICE-Like Protease Activity, and Reactive Oxygen Species", *The Journal of Neuroscience*, 16(15), (1996), 4696-4706.

Sohnlein, P., et al., "Fast and Flexible Setup of Homogeneous Protein Assays Employing 6xHis-Tag Technology—High Sensitivity and Signal-to-Noise Ratios", (Qiagen (r) LiquiChip tm), (Pubilished prior to Jan. 20, 2004), 13 pgs.

Syntichaki, P., et al., "The Biochemistry of Neuronal Necrosis: Rogue Biology?", *Nature Reviews*, 4, 2003 , 672-684.

T, Monsees, et al., "A Novel Bioluminogenic Assay for Alpha-Chymotrypsin", *Journal of Bioluminescence and Chemiluminescence*, 10, Coupled Alpha-Chymotrypsin Assay Abstract, England, (1995), 213-218.

T, Monsees, et al., "Synthesis and Characterization of a Bioluminogenic Substrate for Alpha-Chymotrypsin", *Analytical Biochemistry*, 221, Coupled Alpha-Chymotrypsin Assay Abstract, (1994), 329-334.

Tewari, M., et al., "Yama/CPP32β, a Mammalian Homolog of CED-3, Is a CrmA-Inhibitable Protease That Cleaves the Death Substrate Poly(ADP-Ribose) Polymerase", *Cell*, 81, (Jun. 1995), 801-809.

Thornberry, N. A., et al., "A combinatorial approach defines specificities of members of the caspase family and granzyme B. Functional relationships established for key mediators of apoptosis", *Journal of Biological Chemistry*. 272(29), (Jul. 18, 1997), 17907-17911.

Thornberry, N. A, et al., "A novel heterodimeric cysteine protease is required for interleukin-1β processing in monocytes", *Nature*, 356, (Apr. 1992), 768-774.

Timiryasova, T. M., et al., "Visualization of Vaccinia Virus Infection Using the Renilla-Luciferase-GFP Fusion Protein", *Bioluminescence and Chemiluminescence*, (11th International Proceedings), (2001), 457-460.

Tran, T. V., et al., "Dipeptidyl Peptidase I: Importance of Progranzyme Activation Sequences, Other Dipeptide Sequences, and the N-Terminal Amino Group of Synthetic Substrates for Enzyme Activity", *Archives of Biochemistry and Biophysics*, 403, (2002), 160-170.

Wang, Y., et al., "The Renilla Luciferase-Modified GFP Fusion Protein is Functional in Transformed Cells", *Bioluminescence and Chemiluminescence: Molecular Reporting with Photons*, (Symposium Proceedings,, (1997), 419-422.

White, E. H, et al., "Amino Analogs of Firefly Luciferin and Biological Activity Thereof", *Journal of the American Chemical Society*, 88(7), (1966), 2015-2019.

Wilkinson, J. C., et al., "Upstream Regulatory Role for XIAP in Receptor-Mediated Apoptosis", *Molecular and Cellular Biology*, 24(16), (2004), 7003-7014.

Yewdell, J. W., et al., "Proteasomes get by with lots of help from their friends", (Abstract Only), *Immunity*, 20(4), (2004), 1 pg.

Yu, Y. A., et al., "Inducible Gene Expression in Vivo Using a *Renilla* Luciferase—GFP Fusion Construct", *Bioluminescence and Chemiluminescence*, (11th International Symposium proceedings), (2000), 465-468.

Silva, Jr. F.P. et al., g the subsite specificity of schistsoma mansoni aspartyl hemoglobinase through comparative molecular modeling, FEBS Lett. (2002) 514(2):141-148 (Abstract only).

United States Patent Office Action for U.S. Appl. No. 11/489,978 dated Nov. 28, 2007 (2 pages).

United States Patent Office Action for U.S. Appl. No. 11/510,278 dated Jul. 23, 2009 (19 pages).

United States Patent Office Action for U.S. Appl. No. 11/897,743 dated Oct. 16, 2009 (14 pages).

European Patent Office Action for Application No. 03737580.5 dated Feb. 3, 2009 (4 pages).

Japanese Patent Office Action Decision of Rejection for Application No. 2003-565985 dated Jul. 24, 2009 (4 pages) with English translation.

Japanese Patent Office Action for Application No. 2003-565985 dated Feb. 3, 2009 (7 pages) English translation only.

United States Patent Office Action for U.S. Appl. No. 12/706,078 dated Feb. 18, 2011 (8 pages).

United States Patent Office Action for U.S. Appl. No. 12/146,245 dated Mar. 14, 2011 (10 pages).

Australian Patent Office Action for Application No. 2008239654 dated Mar. 22, 2011 (2 pages).

Chinese Patent Office Action for Application No. 200580008682 dated Jan. 19, 2011 (7 pages).

Moravec, R.A. et al., "Cell-based bioluminescent assays for all three proteasome activities in a homogeneous format," Anal. Biochem. (2009) 287:294-302.

O'Brien, M.A., "A comparison of homogeneous bioluminescent and fluorescent methods for protease assays," Handbook of Assay Development in Drug Discovery (2006) 125-139.

O'Brien, M.A. et al., "Homogeneous, bioluminescent protease assays," Methods in Molecular Biology, vol. 414: Apoptosis and Cancer, G. Mor and A.B. Alvero, editors, Human Press Inc. (2008) 163-181.

Riahi-Madvar, A. et al., "Design and characterization of novel trypsin-resistant firefly luciferases by site-directed mutagenesis," Protein Engineering, Design & Selection (2009) 1-9.

Thompson, J.F. et al., "Mutation of a protease-sensitive region in firefly luciferase alters light emission properties," J. Biol. Chem. (1997) 272(30):18766-18771.

European Patent Office Action for Application No. 05711900.0 dated May 25, 2011 (6 pages).

Takakura, H. et al., "Aminoluciferins as functional bioluminogenic substrates of firefly luciferase," Chemistry an Asian Journal (2011) 6:1800-1810.

United States Patent Office Action for U.S. Appl. No. 12/146,245 dated Jan. 26, 2012 (14 pages).

United States Patent Office Action for U.S. Appl. No. 12/494,100 dated Jan. 9, 2012 (11 pages).

"CaspACE™ Assay System, Colorimetric," Promega website, http://www.promega.com/products/cell-health-assays/apoptosis/fluorometric-and-colorimetric-caspase-assays/caspace-assay-system_-colorimetric/ (Jan. 1, 2000).

European Patent Office Search Report for Application No. 10075526.3 dated Oct. 20, 2011 (8 pages).

United States Patent Office Action for U.S. Appl. No. 12/494,100, dated May 2, 2012 (8 pages).

* cited by examiner

LUMINESCENT LIVE AND DEAD CELL ASSAY

CROSS-REFERENCE TO RELATED APPLICATIONS

This application claims the benefit of the filing date of U.S. application Ser. No. 60/923,376, filed on Apr. 13, 2007, the disclosure of which is incorporated by reference herein.

BACKGROUND

Luminescence is produced in certain organisms as a result of a luciferase-mediated oxidation reaction. Luciferase genes from a wide variety of vastly different species, particularly the luciferase genes of *Photinus pyralis* and *Photuris pennsylvanica* (fireflies of North America), *Pyrophorus plagiophthalamus* (the Jamaican click beetle), *Renilla reniformis* (the sea pansy), and several bacteria (e.g., *Xenorhabdus luminescens* and *Vibrio* spp), are extremely popular luminescence reporter genes. Firefly luciferase is also a popular reporter for determining ATP concentrations, and, in that role, is widely used to detect biomass. Luminescence is also produced by other enzymes when those enzymes are mixed with certain synthetic substrates, for instance, alkaline phosphatase and adamantyl dioxetane phosphate, or horseradish peroxidase and luminol.

Luciferase genes are widely used as genetic reporters due to the non-radioactive nature, sensitivity, and extreme linear range of luminescence assays. For instance, as few as $10^{-20}$ moles of firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays used to determine ATP concentration are highly sensitive, enabling detection to below $10^{-16}$ moles.

Luciferases can generate light via the oxidation of enzyme-specific substrates, e.g., luciferins. For firefly luciferase and all other beetle luciferases, light generation occurs in the presence of magnesium ions, oxygen, and ATP. For anthozoan luciferases, including *Renilla* luciferase, only oxygen is required along with the substrate coelentrazine. Generally, in luminescence assays to determine genetic activity, reaction substrates and other luminescence activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents.

Reporters are useful to detect the presence or activity of molecules within cells or supernatants. For instance, proteases constitute a large and important group of enzymes involved in diverse physiological processes such as protein turnover in blood coagulation, inflammation, reproduction, fibrinolysis, and the immune response. Numerous disease states are caused by, and can be characterized by, the alterations in the activity of specific proteases and their inhibitors. The ability to measure these proteases in research or in a clinical setting is significant to the investigation, treatment and management of disease states. For example, caspase-3 and caspase-7 are members of the cysteine aspartyl-specific protease (also known as the FIX aspartate specific-cysteine protease, "ASCP") family and play key effector roles in cell death in mammalian cells (Thornberry et al., 1992; Nicholson et al., 1995; Tewari et al., 1995; and Fernandes-Alnemri et al., 1996).

Numerous chromogenic and fluorogenic substrates have been used to measure proteases (Monsees et al., 1994; Monsees et al., 1995) and modified luciferins have provided alternatives to fluorescent indicators (U.S. Pat. Nos. 5,035,999 and 5,098,828). Methods for using modified luciferins with a recognition site for a hydrolase as a pro-substrate were first described by Miska and Geiger (1989), where heterogeneous assays were conducted by incubating a modified luciferin with a hydrolase for a specified period of time, then transferring an aliquot of the mixture to a solution containing luciferase. Masuda-Nishimura et al. (2000) reported the use of a single tube (homogeneous) assay which employed a β-galactosidase substrate-modified luciferin.

Experimental treatment of cells in culture can lead to four primary outcomes: cytotoxicity (loss of membrane integrity), cytostatic effects (cell cycle arrest without cytotoxicity), proliferation or no effect versus control. Traditional viability reagents provide the number of viable cells left after treatment, but do not distinguish between cytotoxicity and cytostatic effects. Conversely, cytotoxicity assays provide the relative number of cells that have lost membrane integrity, but not the remaining number of live cells in each well. Because increasingly complex cell models are employed with greater incubation and treatment times, assays are needed to address those problems.

What is needed is an improved assay, e.g., a homogeneous assay, to detect live and dead cells.

SUMMARY OF THE INVENTION

The invention provides a single readout reagent that can determine both the dead cell population and live cell population in a sample. In one embodiment, the reagent is a modified luciferin (a luciferin derivative) which includes a protease substrate. In one embodiment, the modified luciferin reagent is added to a sample and luminescence is employed to measure the dead cell population, then a reagent is added that lyses the remaining live cells while not affecting the modified luciferin reagent chemistry. Luminescence is detected in the lysed sample. The dead cell signal contribution is subtracted from the total luminescence signal to arrive at the live cell signal. Because the luminescent format achieves a signal steady state between dead cell protease activity and luciferase, and the second signal (after intentional lysis) is also collected at steady state, a subtractive method is possible. In contrast, a subtractive method is significantly complicated in product accumulation assays (e.g., fluorescence), because the protease associated with the dead cells continues to contribute to the total fluorescence signal as a function of time. Luminescent assays with exceedingly poor luminescent half-lifes are similarly encumbered. The use of luciferases with longer half-lives, e.g., half-lives of greater than 5 minutes, e.g., a half-life of about 30 minutes, about 2 hours or more, e.g., a half-life of at least 5 hours (see, for example, PCT/US99/30925, the disclosure of which is incorporated by reference herein), provides for "glow" like characteristics of the luciferase readout, thereby addressing those shortcomings.

In one embodiment, the invention provides a bioluminogenic assay where the number of live and dead cells may be detected using a luciferin modified to contain a protease substrate. Preferably, the number of live and dead cells is detected in a single receptacle, e.g., a well of a multi-well plate. As used herein, a "bioluminogenic assay" includes luciferase, a suitable corresponding substrate, e.g., modified forms of luciferin having a protease substrate in which a product of a reaction between the modified luciferin and the protease is a substrate for the luciferase, and one or more other reagents or cofactors, e.g., ATP and/or magnesium. Thus, a bioluminogenic assay of the invention may directly measure the amount or presence of a protease and indirectly measures the number of live and dead cells in a sample and does not rely on the generation of ATP by a nonluciferase mediated reaction. In one embodiment, the luciferase-mediated reaction does not rely on the generation of ATP from the nonluciferase-mediated reaction.

For instance, in one embodiment, a substrate for a luciferase, such as aminoluciferin, which is modified to contain a protease recognition site (modified, for example, via a covalent bond), may be employed in a bioluminogenic assay to detect the protease, i.e., when luciferase is present. The protease to be detected may be a native enzyme or a recombinant enzyme, e.g., including fusion proteins, but is not a secreted enzyme, e.g., it is cytosolic, and the bioluminogenic substrate therefor is viable cell impermeable, i.e., it does not substantially enter (passively or actively) into viable cells. In one embodiment, the protease may be a cysteine protease, a serine protease or an aminopeptidase.

As used herein, a "bioluminogenic assay reagent" includes a bioluminogenic substrate, as well as an optional cofactor(s) or other molecule(s) such as an enzyme for a bioluminogenic reaction. In one embodiment, the bioluminogenic assay reagent may be AAF-aminoluciferin, Z-DEVD-aminoluciferin (SEQ ID NO:1), Z-LETD-aminoluciferin (SEQ ID NO:2), Z-IETD-aminoluciferin (SEQ ID NO:3), Z-DVAD-aminoluciferin (SEQ ID NO:4), or Z-LEHD-aminoluciferin (SEQ ID NO:51. Reagents of various embodiments may include other peptide or polypeptide substrates linked to aminoluciferin, dihydroluciferin, luciferin 6'-methylether, or luciferin 6'-chloroethylether. In other embodiments, the bioluminogenic assay reagent may be another luciferin derivative such as a compound of any one of formulas I-V.

The sample employed in the methods of the invention may be a cell culture or a physiological fluid sample containing cells, e.g., a blood, cerebrospinal fluid, or urine sample. The cells in the sample may be prokaryotic cells or eukaryotic cells.

In one embodiment, the invention provides a method of assaying a protease-mediated bioluminescence reaction to determine the presence or number of live and dead cells in a population of cells, e.g., a cell culture population. The method includes contacting cells with a luciferin modified to contain a protease recognition site. The protease recognition site is specific for a protease that is only present in the extracellular space or supernatant when cell membrane integrity is reduced (compromised) or lost. If the sample contains cells with reduced cell membrane integrity, the protease is released into the extracellular space or supernatant, and the protease cleaves the protease substrate that is coupled to luciferin, yielding a substrate for a luciferase. Luminescence is then detected. The sample is then subjected to reagents or conditions that lyse cells, e.g., detergents, freeze/thaw or sonication, and luminescence is detected. The method may include a two step assay, with reagent adjustment between two reactions. In one embodiment, reagents for a reaction other than for a bioluminogenic assay may be added, and optionally the results for that reaction measured or detected, before or after lysis. Thus, the method may include detecting other activities or molecules before or after lysis.

The invention also provides a method to detect the presence or amount of a modulator, for instance, an inhibitor, of cell viability. In one embodiment, the method includes providing a reaction mixture comprising a bioluminogenic substrate for a protease, reagents for a bioluminescence assay including luciferase, and a test agent. A reaction between the bioluminogenic substrate and the protease yields a product that is a substrate for luciferase, and a reaction between that product and luciferase yields luminescence. The presence or amount of luminescence is compared in test and control reactions. Comparison of the two results indicates the effect of the modulator.

Figure 1A:
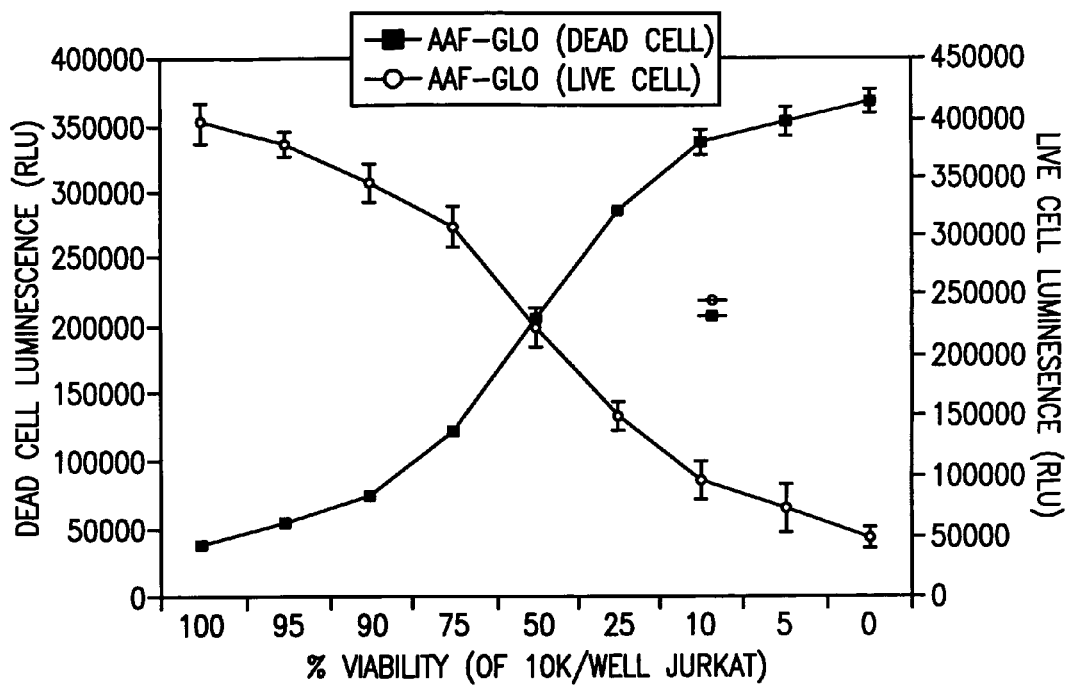
FIGS. 1A-B. CytoTox-Glo Dual Functionality. A) Plot of percent viability versus relative dead cell luminescence and relative live cell luminescence. B) Same data as for panel A but graphed as a % of maximal signal for each response. The $r^2$ were fitted by Excel.

Reduction in viability by cytotoxicity. Viable and cytotoxicity are ratiometric because of the optimal time to measure cytotoxicity. C) Reduction in viability by late-stage cytotoxicity. Viability is reduced because of cytotoxicity. Decline (degradation at highest concentration of cytotoxicity signal) reflects the late stage of cytotoxicity).

DETAILED DESCRIPTION OF THE INVENTION

Definitions

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O) R, —C(=O)R, —C(=O)NRR—S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O) O$_2$RR—P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR) NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

"Stable compound" and "stable structure" are meant to indicate a compound that is sufficiently robust to survive isolation to a useful degree of purity from a reaction mixture. Only stable compounds are contemplated by and claimed in the present invention, however, certain unstable compounds, for example, those that cannot easily be isolated, can be employed in the methods described herein.

One diastereomer may display superior properties or activity compared with another. When required, separation of the racemic material can be achieved by HPLC using a chiral column or by a resolution using a resolving agent such as camphonic chloride as described by Thomas J. Tucker, et al., *J. Med. Chem.* 1994, 37, 2437-2444. A chiral compound may also be directly synthesized using a chiral catalyst or a chiral ligand, e.g. Mark A. Huffman, et al., *J. Org. Chem.* 1995, 60, 1590-1594.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene). The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g., 1, 2, 3, or 4) carbon atoms have been replaced with a heteroatom (e.g., O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The term "amino acid," includes a residue of a natural amino acid (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. *Protecting Groups In Organic Synthesis*, 2$^{nd}$ edition, John Wiley & Sons, Inc., New York (1991) and references cited therein).

The term "peptide" describes a sequence of 2 to 35 amino acids (e.g., as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy, and often a cyclic glycal. The term includes the known simple sugars and their derivatives, as well as polysaccharides with two or more monosaccharide residues. The saccharide can include protecting groups on the hydroxyl groups, as described above in the definition of amino acids. The hydroxyl groups of the saccharide can be replaced with one or more halo or amino groups. Additionally, one or more of the carbon atoms can be oxidized, for example to keto or carboxyl groups.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "linker" as used herein is a carbon chain that covalently attaches two chemical groups together and optionally can self-cleave or if covalently bonded to a substrate for an enzyme, may be cleaved by that enzyme or another molecule, which chain is optionally interrupted by one or more nitrogen atoms, oxygen atoms, carbonyl groups, (substituted) aromatic rings, or peptide bonds.

The term "luciferase," unless specified otherwise, refers to a naturally occurring or mutant luciferase. The luciferase, if naturally occurring, may be obtained easily by the skilled from an organism. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding same. Luciferases are available from Promega Corporation, Madison, Wis.

As used herein, a "bioluminogenic assay" or "bioluminogenic reaction" includes a reaction in which a product of a reaction between a nonluciferase enzyme and a derivative of luciferin or aminoluciferin is a substrate for luciferase or a product of a nonenzymatic reaction having a derivative of luciferin or aminoluciferin is a substrate for luciferase, or a reaction between a luciferase and a derivative of luciferin or aminoluciferin, is bioluminogenic, i.e., produces a measurable amount of light.

As used herein, "bioluminescence" is light produced as a result of a reaction between an enzyme and a substrate that generates light. Examples of such enzymes (bioluminescent enzymes) include firefly luciferase, click beetle luciferase, *Renilla* luciferase, cypridina luciferase, Aequorin photoprotein, obelin photoprotein and the like.

As used herein, a "bioluminogenic assay reagent" may include a substrate, as well as a cofactor(s) or other molecule(s) such as a protein, e.g., an enzyme, for a bioluminogenic reaction.

A "reaction mixture" may contain all reagents for a particular reaction, or may lack at least one of the reagents for the reaction. For example, a luciferase reaction mixture may contain reagents for the reaction except for a substrate for the luciferase, e.g., a reaction mixture useful to determine whether a test sample has a luciferase substrate. A reaction mixture for a nonluciferase enzyme may include all reagents for that reaction except for a molecule to be detected, e.g., the mixture contains all reagents except for a cofactor for the nonluciferase enzyme, and so the mixture is useful to detect the presence of the cofactor in a test sample.

As used herein a "derivative of luciferin" or a "derivative of aminoluciferin" is a molecule that is a substrate for a nonluciferase enzyme and a prosubstrate of a luciferase, a substrate for a luciferase, a substrate for a nonluciferase enzyme and a substrate for a luciferase, or is useful to detect molecules generated in nonenzymatic reactions. The derivatives of the invention have one or more modifications to one or more of the three rings and/or substituents attached to one or more of the rings of the D-luciferin or aminoluciferin backbone.

Methods of the Invention

The methods of the invention are based on proteolytic activities associated with cell membrane permeability and integrity. Advantages of the method include sensitivity, simplicity, and flexibility of assay readout. Measurement of viability is predicated upon the relative impermeability of a bioluminogenic protease substrate and an intracellular protease that is not released from a cell unless membrane integrity is compromised, but that is active in an extracellular environment, e.g., a ubiquitous, conserved intracellular protease. Substrates useful in this embodiment include substrates for exo- or endo-proteases, including substrates that are blocked at the N- or C-terminus. Substantially cell impermeant protease substrates are those which are not detectable in viable cells during a period of time generally employed to measure an endpoint in an assay for dead cells, e.g., at times less than 5, 4, 3, 2 or 1.5 hours, or over 5, 15, 30, 60, or 120 minutes, after addition of the protease substrate to a sample. In one embodiment, a bioluminogenic substantially cell impermeable substrate includes an amino acid, or a di- or tri-peptide substrate. In one embodiment, a bioluminogenic cell impermeable substrate is a substrate for a tripeptidyl peptidase, calpain or chymotrypsin, and a prosubstrate for luciferin.

Accordingly, the use of the live and dead cell assay described herein provides for inverse and complimentary measures of cell health, and can be employed to detect the effect of alterations in conditions, for instance, treatment with a compound. Further, protease activity has practical sensitivities (detection of <2-5% difference in viability in 10,000 cells/well), which sensitivities can be achieved in a few minutes. In addition, the substrate(s) may be admixed into cell wells without dramatically altering the well volume, which increases the flexibility of next step endpoint chemistries.

The invention thus provides a method to detect live and dead cells in a sample. The method includes contacting a sample with a bioluminogenic substantially cell impermeant substrate for a protease. The sample is optionally treated with one or more test conditions or agents. A reaction with the substrate mediated by the protease yields a product that is a substrate for luciferase, and a reaction with the substrate mediated by the protease after lysis yields the same substrate. Luminescence in the sample is detected before and after lysis, which in turn detects the number or presence of dead and live cells, respectively, in the sample.

The invention provides an assay method in which dead and live cells are detected in a sample using the same reagent, i.e., a reagent altered by a protease. The resulting signal for each reaction is related to the presence or amount of the protease in the sample before and after lysis.

In one embodiment, the protease and luciferase assays are carried out in tandem. For instance, a luciferin derivative is added to a sample under conditions allowing for a protease reaction but not for a luciferase reaction, e.g., luciferase is not present. Then one or more reagents for a luciferase reaction are added and luminescence is detected. The mixture is then subjected to a lysing reagent or conditions that result in lysis. Luminescence is again detected.

The assays of the present invention allow for the detection of live and dead cells in a sample, e.g., a sample which includes eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a protease detected by the methods of the invention, a moiety which alters the level or activity of the protease, and/or a gene product unrelated to the molecule or moiety that alters the level or activity of the protease, or a gene product unrelated to the protease.

In one embodiment, the methods according to the present invention provide a rapid, highly sensitive method for detecting dead and live cells in a single sample such as an aliquot of cells. In one embodiment, the method includes quantifying the presence or amount (activity) of the protease, e.g., an exo- or endo-protease, in a bioluminogenic assay. In one embodiment, the present invention relates to a method of measuring the presence or amount of one protease in a single aliquot of cells. In one embodiment, the protease is an endogenous protease. For example, in one embodiment, the present invention provides an improved, sensitive method for monitoring the activity of at least one native protease in preparations including purified preparations of prokaryotic or eukaryotic cells, such as cultured eukaryotic cells, e.g., mammalian cells. In one embodiment, a cell impermeant substrate for an intracellular protease is added to a sample comprising cells that has not been subjected to lysis but may have been subjected to test agents or conditions, luminescence is detected, and the cells are then lysed, and luminescence detected. The intensity of the bioluminogenic signal is a function of the presence or amount of the protease.

The use of the luciferin derivatives described herein can result in an assay which produces a measurable change in optical properties upon interaction with the protease, which interaction alters the structure of the luciferin derivative. The product of a reaction between a luciferin derivative and the protease need not be D-luciferin or aminoluciferin. For example, a luciferin derivative may include a substrate that includes a reactive chemical group for a protease linked to luciferin or aminoluciferin via a chemical linker. Transformation of the reactive chemical group of the derivative by the protease may yield a product that contains (retains) a portion of the substrate, a portion of the chemical linker, the chemical linker, or a portion of the substrate and the chemical linker, and that product is a substrate for luciferase. Also provided are luciferin derivatives which, after interaction with a protease, may yield a product that optionally undergoes one or more further reactions, e.g., β-elimination, to yield a suitable substrate for luciferase. Luciferin derivatives in which the backbone of luciferin is further modified in its ring structure, e.g., a quinolyl or napthyl luciferin, are provided, as well as providing modifications at the carboxy position of the thiazole ring.

Exemplary cleavage sites for some proteases are set forth in Table 1.

TABLE 1

| Protease | Cut Site(s) |
| --- | --- |
| Aminopeptidase M | Hydrolysis from free N-terminus |
| Carboxypeptidase Y | Hydrolysis from C-terminus |
| Caspase-1,4,5 | W/LEHD-X (SEQ ID NO:6) |
| Caspase-2,3,7 | DEXD-X (SEQ ID NO:7) |
| Caspase-6,8,9 | L/VEXD-X (SEQ ID NO:8) |
| Chymotrypsin | Y-X, F-X, T-X, (L-X, M-X, A-X, E-X) |
| Factor Xa | IEGR-X (SEQ ID NO:19) |
| Pepsin | F-Z, M-Z, L-Z, W-Z (where Z is a hydrophobic residue) but will cleave others |
| TEV | E(N)XYXQ-S/G (SEQ ID NO:9) |
| Thrombin | R-X |
| Trypsin | R-X, K-X |
| Tryptase | PRNK-X (SEQ ID NO:10) |
| β-secretase | EISEVK/NM/L-DAEFRHD, (SEQ ID NO:11), e.g., SEVNL-DAEFR (SEQ ID NO:12) |

X is one or more amino acids

Exemplary protease substrates include, but are not limited to, Z-LLVY (SEQ ID NO:13), AAF, Z-LR, Z-FR, GF, F, Y, Z-GAM, D-ALK (SEQ ID NO:14), GA, GG, Z-RLRGG (SEQ ID NO:15), Z-LRGG (SEQ ID NO:16), AAY, PFR, GGL, SY, FR, and RPFHLLVY (SEQ ID NO:17), and exemplary proteases include but are not limited to those in Table 2.

TABLE 2

| Substrate: | Target Protease(s) |
| --- | --- |
| Z-Phe-Arg- | Cathepsin B, L |
| Z-Gly-Gly-Leu- | 20S Proteasome |
| Z-Arg-Leu-Arg-Gly-Gly- (SEQ ID NO:15) | Isopeptidase T |
| Z-Leu-Arg-Gly-Gly- (SEQ ID NO:16) | Isopeptidase T |
| S-R-P-F-H-L-V-Y- | Proteosome, Chymotrypsin |
| H-Pro-Phe-Arg- | Kallikrein |
| H-Gly-Gly- | Aminopeptidase |
| H-Gly-Ala- | Aminopeptidase |
| H-D-Ala-Leu-Lys- (SEQ ID NO:14) | Plasmin |
| Ala-Ala-Phe- | Tripeptidyl Peptidase II |
| Gluty-Ala-Ala-Phe- (SEQ ID NO:18) | Chymotrypsin |
| Gly-Phe- | Cathepsin C |
| Suc-Leu-Leu-Val-Tyr- (SEQ ID NO:13) | Calpain, Chymotrypsin |
| Z-Leu-Leu-Val-Tyr- (SEQ ID NO:13) | Calpain, Chymotrypsin |
| Z-Gly-Ala-Met- | |
| Ac-Ala-Ala-Tyr- | Chymotrypsin |
| Z-Leu-Arg- | Cathepsin K |
| Z-Phe-Arg- | Cathepsin B, L |
| Ser-Tyr- | Aminopeptidase |

TABLE 2-continued

| Substrate: | Target Protease(s) |
| --- | --- |
| H-Phe- | Aminopeptidase M |
| H-Tyr- | ApM or Cathepsin H |
| Suc-Ala-Ala-Phe- | Chymotrypsin |

In one embodiment, the protease is detected using a substrate which includes an amino-modified luciferin or a carboxy protected derivative thereof, which modification includes a substrate for a protease. In another embodiment, the modification is up to three or four amino acid residues which include a recognition site for a protease. In one embodiment, the substrate is covalently linked to the amino group of aminoluciferin or a carboxy-modified derivative thereof via a peptide bond. In one embodiment, the N-terminus of a peptide or protein substrate is modified to prevent degradation by aminopeptidases, e.g., using an amino-terminal protecting group. In the absence of the appropriate protease or cofactor, a mixture including such a substrate and luciferase generates minimal light as minimal aminoluciferin is present. In the presence of the appropriate protease, the bond linking the substrate and aminoluciferin can be cleaved by the enzyme to yield a substrate for luciferase. Thus, in the presence of luciferase, for instance, a native, recombinant or mutant luciferase, and any cofactors and appropriate reaction conditions, light is generated, which is proportional to the presence or activity of the protease.

In one embodiment, regardless of whether protease- and luciferase-mediated reactions are initiated at the same time or not, luminescence is detected after the luciferase-mediated reaction is initiated. In other embodiments, the reactions are initiated essentially simultaneously. In one embodiment, a reaction specific for a molecule other than the protease is initiated, and the presence or activity of that molecule detected prior to the protease-based assay, and optionally the reaction for the molecule is substantially decreased prior to detecting the presence or amount of the protease, e.g., by waiting until the first signal has diminished, e.g., by at least 50%, or by adding a quenching agent for the first reaction. Thus, a bioluminogenic reaction of the invention can be combined with other assays, so long as the other assay does not interfere with cell viability or interfere with detection (quantification) of luminescence. Thus, in some embodiments, one or more of the reactions are terminated, e.g., by inhibiting an enzyme for the reaction, prior to detection of the protease. Preferably, the signal produced by one assay does not substantially interfere with the quantification of the signal produced by at least one other assay.

Luciferin Derivatives Useful in the Methods

Modifications of luciferin within the scope of the derivatives of this invention include one or more substitutions of a ring atom, one or more substitutions of a substituent (atom or group) attached to a ring atom, and/or addition of one or more atoms to the ring, e.g., expansion or addition of rings, or a combination thereof, at least one of which modifications includes a protease substrate. Native firefly luciferin has three linked rings, a 6 membered 'benzo' ring having an OH group at position 6 ("ring A" or "A ring" hereinafter), a 5 membered thiazole ring fused to the 6 membered benzo ring ("ring B" or "B ring" hereinafter), and a 5 membered thiazole ring that is modified with a carboxyl group at position 5 ("ring C" or "C ring" hereinafter).

For instance, a luciferin derivative with an A ring modification may have a substitution of a C atom in the A ring with another atom, addition of a ring, a substitution of a substituent attached to a ring atom with a different atom or group, or any combination thereof, one of which may include a protease substrate. A luciferin derivative with a B ring modification may have an addition to, or substitution of, an atom in the five membered ring, e.g., insertion of one or more atoms, thereby expanding the ring, for instance, to a six membered ring, substitution of N or S in the ring with a different atom, e.g., a C or O, substitution of a substituent atom or group attached to a ring atom, or any combination thereof, one of which may include a protease substrate.

A luciferin derivative with a C ring modification may have a substitution of an atom in the ring with another atom, a substitution of a substituent attached to a ring atom, with a different atom or group, or any combination thereof, one of which may include a protease substrate. In one embodiment, a derivative of the invention is one which is modified at more than one position, for instance, the derivative has two (or more) A ring modifications, two (or more) B ring modifications, two (or more) C ring modifications, or any combination thereof, one of which includes a protease substrate. In one embodiment, the derivative includes the substitution of a substituent on one of the rings of D-luciferin with a substrate for a protease, or a linker and a substrate for the protease.

In one embodiment, the invention provides a compound of formula I:

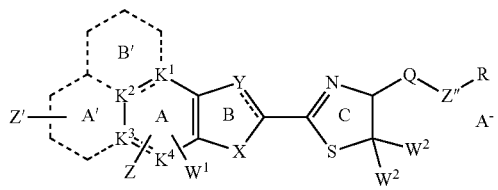

(I)

wherein
Y is N, N-oxide, N—($C_1$-$C_6$)alkyl, or CH;
X is S, O, CH=CH, N=CH, or CH=N;
Z and Z' are independently H, R, OR, SR, NHR, or NRR;
Z" is O, S, NH, NHR, N=N;
Q is carbonyl, $CH_2$, or a direct bond;
$W^1$ is H, halo, ($C_1$-$C_6$)alkyl, ($C_2$-$C_{20}$)alkenyl, hydroxyl, ($C_1$-$C_6$)alkoxy; or
$W^1$ and Z are both keto groups on ring A, and at least one of the dotted lines denoting optional double bonds in ring A is absent;
each $W^2$ is independently H, halo, ($C_1$-$C_6$)alkyl, ($C_2$-$C_4$)alkenyl, hydroxyl, ($C_1$-$C_6$)alkoxy;
each of $K^1$, $K^2$, $K^3$, and $K^4$ are independently CH, N, N-oxide, or N—($C_1$-$C_6$)alkyl;
the dotted lines in ring A and ring B denote optional double bonds;
A' and B' are optionally present aromatic rings fused to ring A, only one of which is present in the compound, so as to form a fused tricyclic system, and when A' or B' is present, the group Z' is an optionally present substituent of either ring A' or ring B';
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroarylsulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_1$-$C_{20}$)acyl, ($C_1$-$C_{20}$)acyloxy, ($C_1$-$C_{20}$)alkylthio, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, a chain of one to about ten amino acids, or $M^+$ optionally when Z" is oxygen, wherein M is an alkali metal;
or when Z or Z' is NRR, RR together with N form a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents comprising ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxyl, ($C_1$-$C_{20}$)alkylcarbonyl, ($C_1$-$C_{20}$)alkylcarboxyl, halo, hydroxyl, —COO$R^x$, —SO$_2R^x$, —SO$_3R^x$, nitro, amino, ($C_1$-$C_{20}$)alkyl-S(O)—, ($C_1$-$C_{20}$)alkyl-SO$_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, or heterocycle, wherein each substituent is optionally substituted with one to three R groups;
$R^x$ is H, ($C_1$-$C_6$)alkyl, or ($C_6$-$C_{30}$)aryl; and
wherein at least one Z or Z', e.g., the R group of Z or Z', is a group of or a chain of one to about ten amino acids; or a salt thereof.

In various embodiments, when Y is N, then X is not S. In other embodiments, when X is S, then Y is not N;

When Z or Z' comprises a nitrogen moiety, one or both of the hydrogens of the Z or Z' nitrogen moiety may be replaced by ($C_1$-$C_{20}$)alkyl or the group L, wherein L is an amino acid radical, a peptide radical having up to 20 amino acid moieties, or any other small molecule that is a substrate for a protease. In certain embodiments, when L is an amino acid radical or a peptide radical, at least one $W^2$ is not H.

When Z is a hydroxyl group or a nitrogen moiety, H of the hydroxyl or nitrogen moiety may be replaced by a chain of one to ten amino acids, (HO)$_2$P(O)—OCH$_2$—, sulfo, —PO$_3$H$_2$, or by a cephalosporanic acid, attached to the group Z via a carbon chain of one to about 12 carbon atoms. In certain embodiments, when ring B is a thiazole ring, the sulfo or the —PO$_3$H$_2$ group is attached to the hydroxyl oxygen via a ($C_1$-$C_6$)alkylene group.

When Z or Z' is a hydroxyl group or a nitrogen moiety, or when Z"—R is a hydroxyl group, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonding groups (amides).

The group 'linker' can be attached to L' via an oxygen atom or an NH group at one terminus of the linker and the other terminus of the linker can form an ether, ester, or amide linkage with a group Z, Z', or Z"—R.

When Z is OR, formula (I) is optionally a dimer connected at the two A rings via a linker comprising a ($C_1$-$C_{12}$)alkyl diradical that is optionally interrupted by one to four O atoms, N atoms, or an optionally substituted aryl, heteroaryl, or heterocycle group to form a bridge between the dimer of formula (I), and the R group of each Z group connecting the dimer of formula (I) is replaced by the bridge. In certain embodiments, a saccharide is not directly attached to $K^3$.

The group "$A^-$" is an anion, present when a quaternary nitrogen is present. The compounds of formula I also include other salts besides quaternary ammonium salts, such as those salts described above.

In various embodiments, when rings A and B form a naphthalene or quinoline ring system, then $W^1$ is not hydrogen; when a ring A substituent is OH, then —Q-Z"—R is not —C(O)—NH—NH$_2$; when Y is N or CH and X is CH=CH and $W^1$ is H, then Z is not OH attached to $K^3$; and/or when Y is N or CH and X is CH=CH and Z is H, then $W^1$ is not OH attached to $K^3$.

In another embodiment, the invention provides a compound of formula (II):

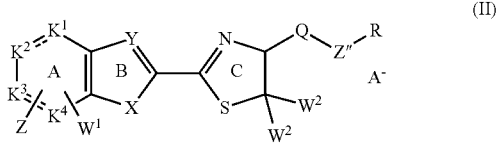

(II)

wherein X, Y, Z, Z", $K^1$-$K^4$, $W^1$, $W^2$, $A^-$, and R are as defined for compounds of formula I.

In another embodiment, the invention provides a compound of formula (III):

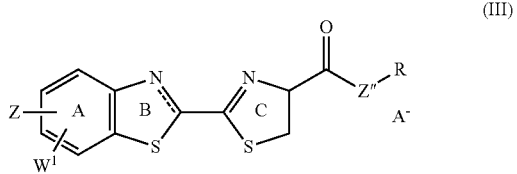

(III)

wherein Z, Z", $W^1$, $A^-$, and R are as defined for compounds of formula I.

Also provided is a compound of formula (IV):

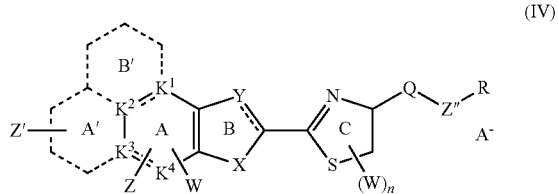

(IV)

wherein
Y is N, N-oxide, N-loweralkyl, or CH;
X is S, CH=CH, or N=C,
Z and Z' are independently H, OR, NHR, NRR, or a cyclic dioxaborolane group attached to ring A or A' via the boron atom;
Z" is O, S, NH, NHR, or N=N;
each W is independently H, halo, $C_{1-6}$alkyl, $C_{2-20}$alkenyl, hydroxyl, or $C_{1-6}$alkoxy; or
W and Z are both keto groups on ring A, and the dotted lines in ring A are absent;
each of $K^1$, $K^2$, $K^3$, and $K^4$ are independently CH, N, N-oxide, or N-loweralkyl;
the dotted lines in ring A and ring B denote optional double bonds;
each R is independently H, amino, $C_{1-20}$alkyl, $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$alkyl, $C_{1-12}$alkoxy, $C_{1-12}$alkoxycarbonyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, tri$C_{1-20}$ ammonium$C_{1-20}$alkyl, $C_{6-30}$arylsulfoxy, heteroaryl$C_{1-20}$alkyl, heteroaryl having quaternary nitrogen, heteroarylcarbonyl having quaternary nitrogen, N-methyl-tetrahydropyridinyl, or pentafluorophenylsulfonyl;

wherein any alkyl, alkenyl, alkynyl, cycloalkyl, alkoxy, aryl, heteroaryl, heterocycle, or amino group can be optionally substituted by one or more, e.g., 1, 2, 3, 4, or 5, $C_{1-20}$alkyl, $C_{2-20}$alkenyl, $C_{3-20}$alkynyl, $C_{3-20}$cycloalkyl, halo, hydroxyl, acyl, acyloxy, —COOR$^1$, —SO$_3$R$^1$, amino, nitro, lower alkylamino, lower alkynylamino, imidazolinyl-methylamino, di-lower alkylamino, di-lower alkynylamino, piperidino, pyrrolidino, azetidino, aziridino, di-imidazolinylmethyl-amino, mercapto, $C_{1-20}$alkylthio, $C_{6-30}$arylthio, trifluoromethyl, $C_{1-20}$alkylcarboxyl, $C_{6-30}$aryl, $C_{6-30}$aryl$C_{1-20}$alkoxyl, heteroaryl, heterocycle, heterocycle $C_{1-20}$alkyl, or $C_{6-30}$aryl $C_{1-20}$alkyl carbonyl; and wherein each group R is defined independently if more than one is present;

$R^1$ is hydrogen, $C_{1-6}$alkyl, or $C_{6-30}$aryl;
Q is C(=O), CH$_2$, or a direct bond;
n is 0, 1, or 2;
wherein at least one Z or Z', e.g., the R group of Z or Z', is a group of or
chain of one to about ten amino acids and
$A^-$ is an anion, present when a quaternary nitrogen is present; or a salt thereof.

In certain embodiments, when Z or Z" is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a protease. When L is an amino acid radical or a peptide radical, W is not H in certain embodiments.

In various embodiments, when Z is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms. In certain embodiments, when ring B is a thiazole ring, the sulfo or the —PO$_3$H$_2$ group can be attached to the hydroxyl oxygen via a loweralkylene chain.

In certain embodiments, when Z or Z' is hydroxyl or amino or when Z"—R is hydroxyl, one H of the hydroxyl or amino may be replaced by the group L'- linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and linker is attached to L' via an oxygen atom or an NH group at one terminus of the linker and the other terminus of the linker forms an ether, ester, or amide linkage with the group Z, Z', or Z"—R.

In certain embodiments, when Z is OR, formula (IV) can optionally be a dimer connected at the two A rings via a CH$_2$ or CH$_2$—C$_6$H$_4$—CH$_2$ bridge, and the R group of each Z group connecting the dimer of formula (IV) can be replaced by the bridge.

In certain embodiments, A' and B' are optional aromatic rings fused to ring A, only one of which may be present at a time, so as to form a fused tricyclic system; and when B' is present, the group Z is present, and when A' is present, the group Z is absent. In certain embodiments, one carbon of ring A may be replaced by an N-oxide moiety. In certain embodiments, if X is N=C, ring C can optionally be attached at the carbon atom of the N=C moiety. In certain embodiments, W is not hydrogen when the compound to which W is attached is luciferin, luciferin methyl ester, or aminoluciferin or when rings A and B form a naphthalene or quinoline ring system. In certain embodiments, -Q-Z"—R is not —C(O)—NH—NH$_2$ when a ring A substituent is OH.

In one embodiment, the W group attached to ring C is absent (i.e., the value of "n" is 0). In another embodiment, the W group attached to ring C is H or F.

In one embodiment, the invention provides a compound of formula V:

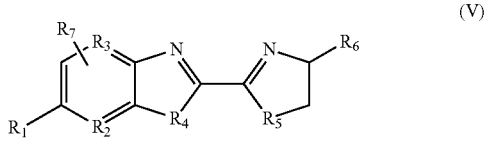

(V)

wherein

R$_1$ is hydrogen, hydroxyl, amino, C$_{1-20}$ alkoxy, substituted C$_{1-20}$ alkoxy, C$_{2-20}$ alkenyloxy, substituted C$_{2-20}$ alkenyloxy, halogenated C$_{2-20}$ alkoxy, substituted halogenated C$_{2-20}$ alkoxy, C$_{3-20}$ alkynyloxy, substituted C$_{3-20}$ alkynyloxy, C$_{3-20}$ cycloalkoxy, substituted C$_{3-20}$ cycloalkoxy, C$_{3-20}$ cycloalkylamino, substituted C$_{3-20}$ cycloalkylamino, C$_{1-20}$ alkylamino, substituted C$_{1-20}$ alkylamino, di C$_{1-20}$ alkylamino, substituted diC$_{1-20}$ alkylamino, C$_{2-20}$ alkenylamino, substituted C$_{2-20}$ alkenylamino, di C$_{2-20}$ alkenylamino, substituted di C$_{2-20}$ alkenylamino, C$_{2-20}$ alkenyl C$_{1-20}$ alkylamino, substituted C$_{2-20}$ alkenyl C$_{1-20}$ alkylamino, C$_{3-20}$ alkynylamino, substituted C$_{3-20}$ alkynylamino, di C$_{3-20}$ alkynylamino, substituted di alkynylamino, C$_{3-20}$ alkynyl C$_{2-20}$ alkenylamino, substituted C$_{3-20}$ alkynyl C$_{2-20}$ alkenylamino, or a chain of one to about ten amino acids;

R$_2$ and R$_3$ are independently C or N;

R$_4$ and R$_5$ are independently S, O, NR$_8$;

R$_6$ is CH$_2$OH, COR$_{11}$, or —OM$^+$ wherein M$^+$ is an alkali metal or a pharmaceutically acceptable salt;

R$_7$ is H, C$_{1-6}$ alkyl, C$_{1-20}$ alkenyl, halogen, or C$_{1-6}$ alkoxide;

R$_8$ is hydrogen, C$_{1-20}$ alkyl, CR$_9$R$_{10}$ wherein R$_9$ and R$_{10}$ are independently H, C$_{1-20}$ alkyl, or fluorine;

R$_{11}$ is H, OH, C$_{1-20}$ alkoxide, C$_{2-20}$ alkenyl, or NR$_{12}$R$_{13}$ wherein R$_{12}$ and R$_{13}$ are independently H or C$_{1-20}$ alkyl; and wherein at least one chain of one to about ten amino acids is present in the compound of formula V such that the compound is a protease substrate.

In one series of embodiments that include formula I above, R$_1$ is not OH or NH$_2$, R$_7$ is not H, R$_6$ is not COR$_{11}$, R$_{11}$ is not OH, R$_3$ and R$_2$ are not both carbon, and R$_4$ and R$_5$ are not both S at the same time.

The invention will be further described by the following non-limiting examples. For all examples, suitable control reactions are readily designed by those skilled in the art.

Example I

To determine whether a single protease substrate could be employed to detect live and dead cells, Jurkat cells were adjusted to 100,000 cells/ml in RPMI 1640+10% FBS. The sample was split into two volumes. One volume was subjected to mild sonication to simulate cytotoxicity. The other volume was left untreated. The sonicated (dead) and untreated (live) volumes were combined in various ratios to represent 100, 95, 90, 75, 50, 25, 10, 5, and 0% viability. Each blend was added to a microtiter well in replicate 100 µA volumes (10,000 cell/well equivalents). CytoTox-Glo Reagent (2× reagent is comprised of 100 µM AAF-aminoluciferin "AAF-Glo substrate", 100 mM Hepes, 50 mM MgSO$_4$ pH 7.5 and used to rehydrate a luciferin detection reagent "cake" which includes lyophilized luciferase, a binding agent and ATP) was prepared and added to each well in a equal volume (100 µL) per well. The plate was incubated at room temperature for 15 minutes and the dead cell signal measured using a BMG PolarStar. Digitonin (20 mg/mL in DMSO) was diluted to 300 µg/mL in CytoTox-Glo buffer (100 mM Hepes and 50 mM Mg SO$_4$) and added in 20 µL volumes per well to facilitate complete cellular lysis. Luminescence was measured after 15 minutes of incubation at room temperature.

Figure 1B:
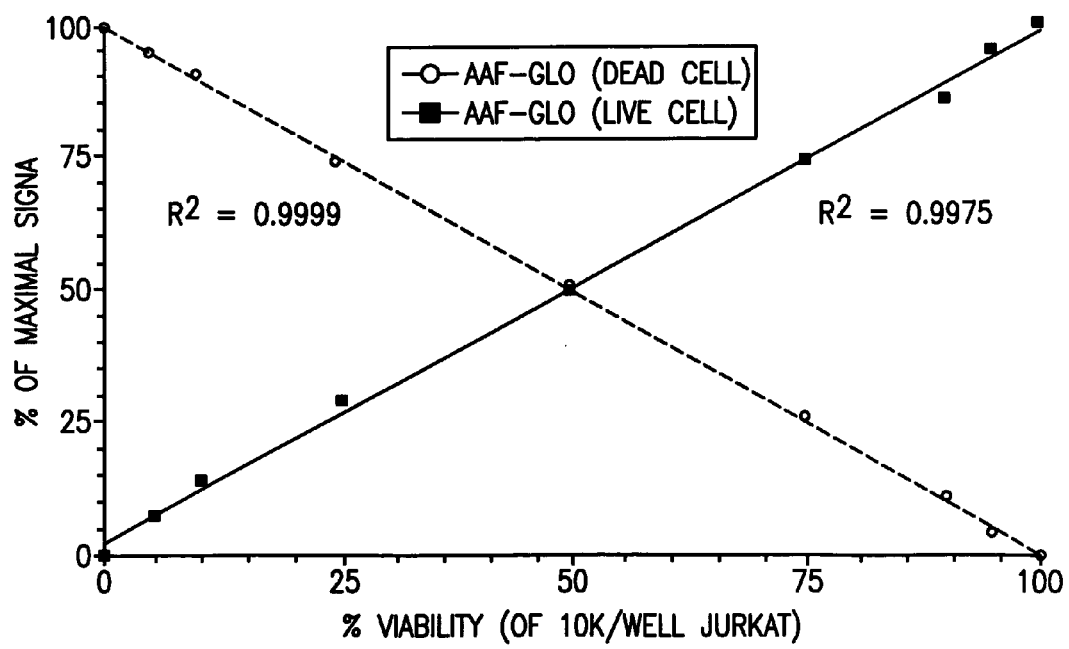

The luminescent signal collected after lysis was adjusted to reflect the "live cell" contribution by subtracting the initial dead cell signal (FIG. 1A). The data in FIG. 1A were plotted as the dead and "live cell" signals versus the % viability. FIG. 1B is the same data as in FIG. 1A, but graphed as a % of maximal signal for each response.

A. Nocodazole Data

Hela cells were seeded at a density of 10,000 cells/well in DMEM+10% FBS in 50 µL volumes and allowed to attach overnight at 37° C. in 5% CO$_2$. Nocodazole (an anti-neoplastic agent) was two-fold serially diluted in DMEM+10% FBS in a separate plate from 2 µM and added in 50 µL it volumes (highest final dosage is 1000 nM). The cells were incubated with the compound for 24 hours. CytoTox-Glo Reagent was prepared as above and added to each well in a equal volume (100 µL) per well. After 15 minutes of incubation, the dead cell signal was collected. Digitonin was added to 30 µg/mL in wells containing the AAF-Glo reagent. CellTiter-Glo was prepared by rehydrating the cake with provided buffer, then added in 100 µL volumes per well. The plate was shaken using an orbital shaker at 700 RPM to ensure homogeneity.

Figure 2A:
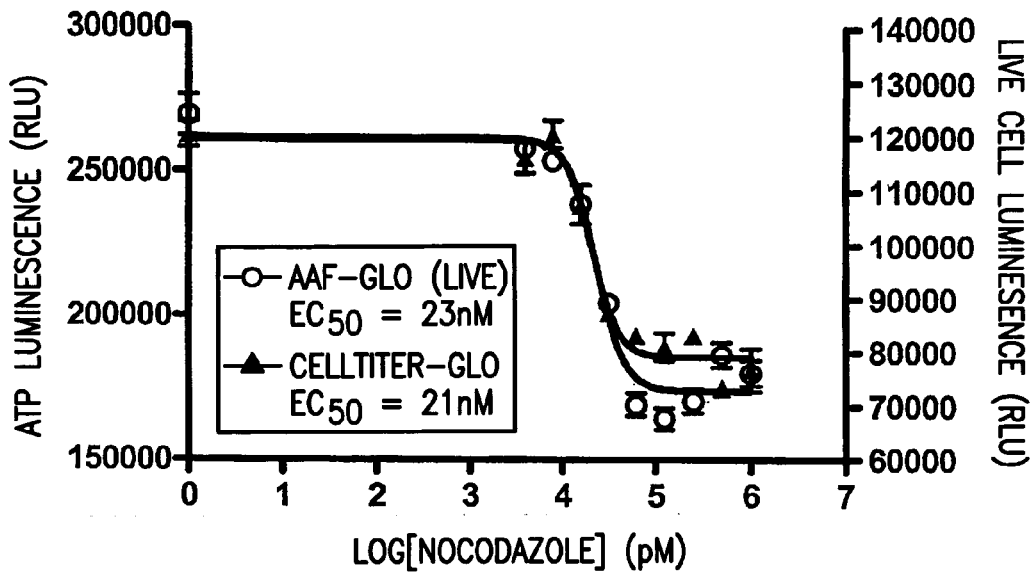
FIGS. 2A-B. A) Plot of log nocodazole versus relative ATP luminescence versus and relative live HeLa cell luminescence (24 hour treatment). B) Plot of log paclitaxel versus relative ATP luminescence and relative live HeLa cell luminescence (24 hour treatment).

The resulting luminescent signals were collected using a BMG Polarstar (FIG. 2A). The dead cell signal was subtracted from the digitonin treated signal and plotted versus CellTiter-Glo using GraphPad Prism. The significance of the data is that the cytotoxic signal (not shown) and the live cell data using CytoTox-Glo corresponds nicely to CellTiter-Glo data, which only provides the remaining cell values.

B. Paclitaxel and Colchicine Data

Figure 2B:
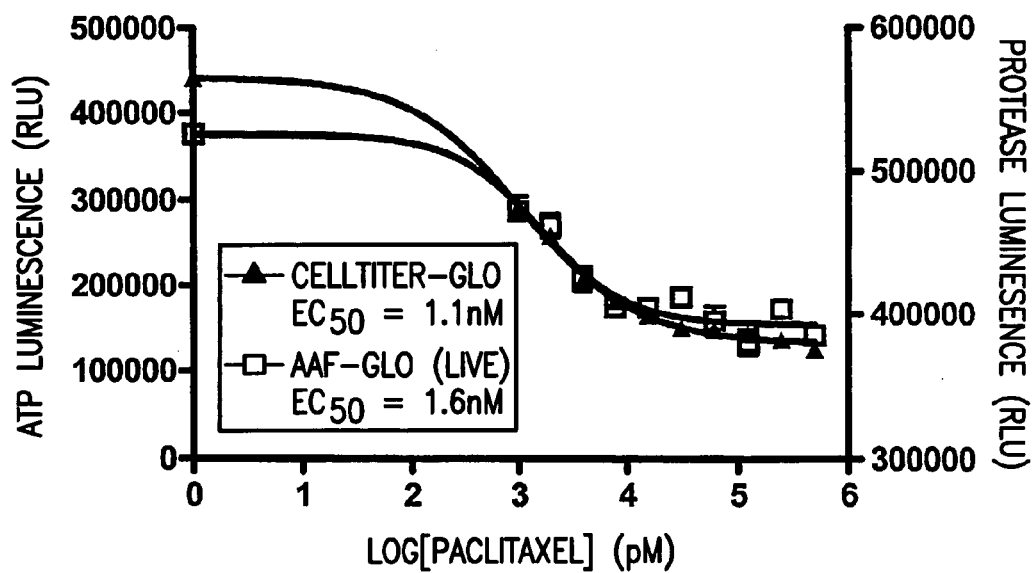

FIG. 2B shows data for paclitaxel (mitosis inhibitor), where the highest dosage was 500 nM. Again, the values derived from CellTiter-Glo and Cytotox-Glo were similar with a mechanistically different toxic insult.

Figure 3:
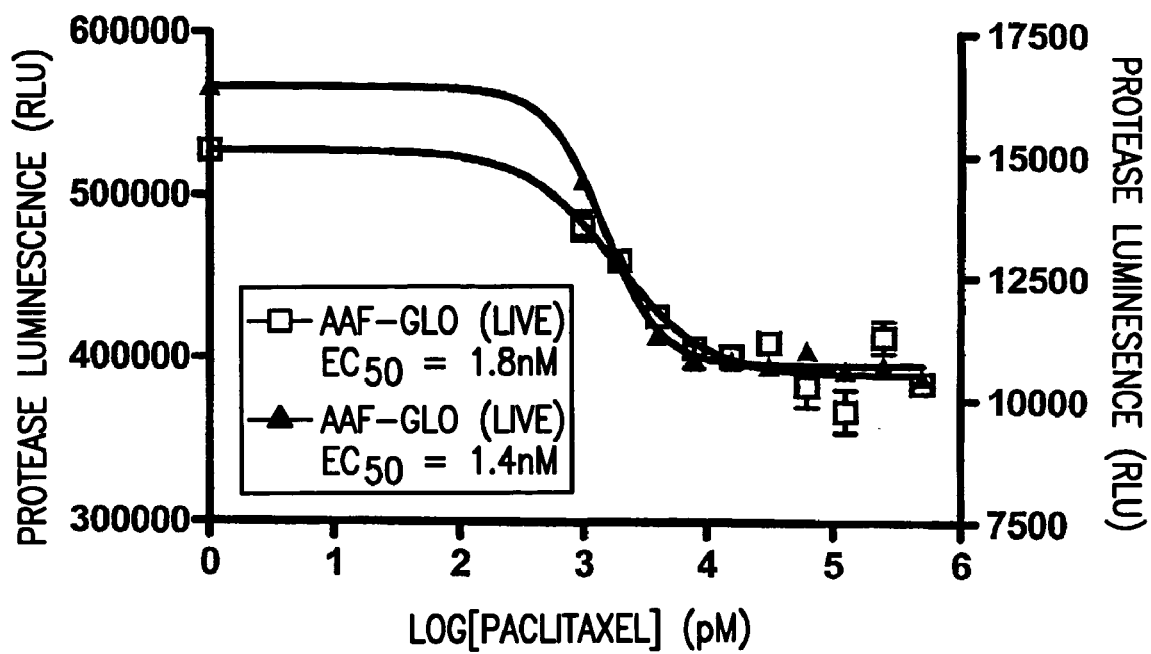
FIG. 3. Plot of log paclitaxel versus relative protease luminescence and relative protease fluorescence in HeLa cells (24 hour treatment).

FIG. 3 shows data with paclitaxel (the highest dosage being 500 nM) and GF-AFC (a live cell substrate). GF-AMC was diluted to 200 µM in 100 mM HEPES with 50 mM MgSO$_4$ pH 7.5 and added to each well in 50 µL volumes. After 30 minutes of incubation at 37° C., the live cell fluorescence values were collected using a BMG Polarstar. CytoTox-Glo Reagent was prepared as a 2× reagent and added in 100 µL volumes. The dead cell values were collected using the BMG Polarstar after 15 minutes of incubation at room temperature. Digitonin was added to 30 µg/mL in a 20 µL volume and the plate shaken using an orbital shaker. The digitonin treated luminescence was measured using the BMG Polarstar.

The dead cell luminescence was subtracted from the digitonin treated luminescence and plotted versus the live cell fluorescence values using GraphPad Prism. The live cell data was comparable using completely different methods and markers for viability (compare FIGS. 2 and 3).

C. Actinomycin D and Colchicine Data

Actinomycin D (anti-tumor antibiotic) was two-fold serially diluted in RPMI 1640+10% FBS from 2 µM in 50 µL volumes in a microwell plate. RPMI 1640+10% FBS served as the uninduced control. Jurkat cells were added to 10,000 cells/well in 50 µL volumes. The plate was mixed by orbital shaking, then incubated at 37° C. in 5% CO$_2$ for 24 hours.

GF-AFC was diluted to 200 µM in 100 mM HEPES with 50 mM MgSO$_4$ pH 7.5 and added to each well in 50 µL volumes. After 30 minutes of incubation at 37° C., the live cell fluorescence values were collected using a BMG Polarstar. CytoTox-Glo Reagent was prepared as a 2× reagent and added in 100 µL volumes. The dead cell values were collected using the BMG Polarstar after 15 minutes of incubation at room temperature. Digitonin was added to 30 µg/mL in a 20 µL volume and the plate shaken using an orbital shaker. The digitonin treated luminescence was measured using the BMG Polarstar.

Figure 4A:
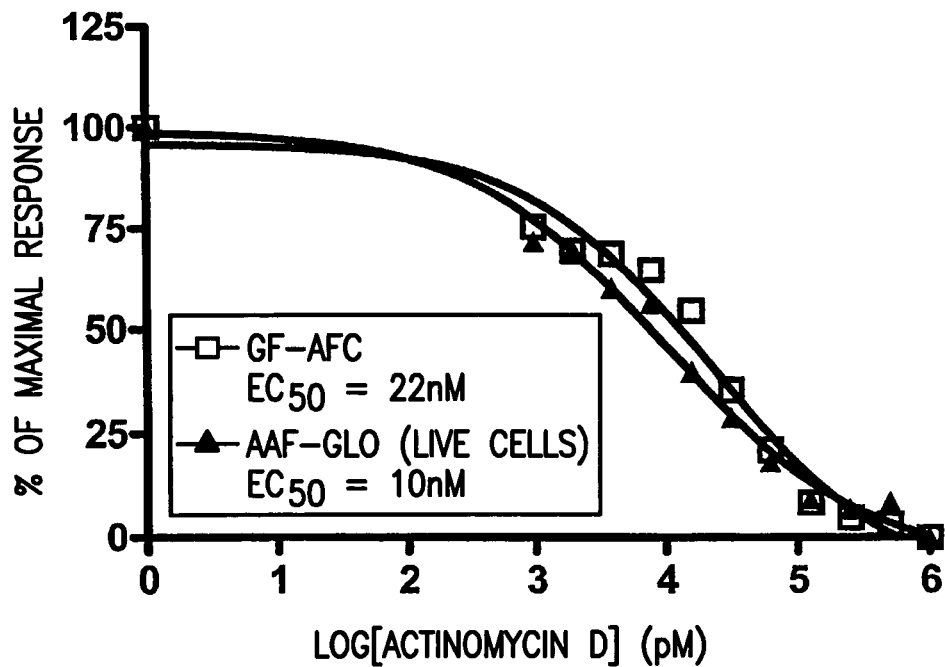
FIGS. 4A-B. A) Plot of log actinomycin D versus percent of maximal response in Jurkat cells (24 hours). B) Plot of log colchicine versus relative protease luminescence and relative protease fluorescence in HeLa cells (24 hour treatment).

The dead cell luminescence was subtracted from the digitonin treated luminescence and plotted versus the live cell fluorescence values (as a % of maximal signal) using GraphPad Prism (FIG. 4A). The live cell data was comparable using completely different methods and markers for viability.

Figure 4B:
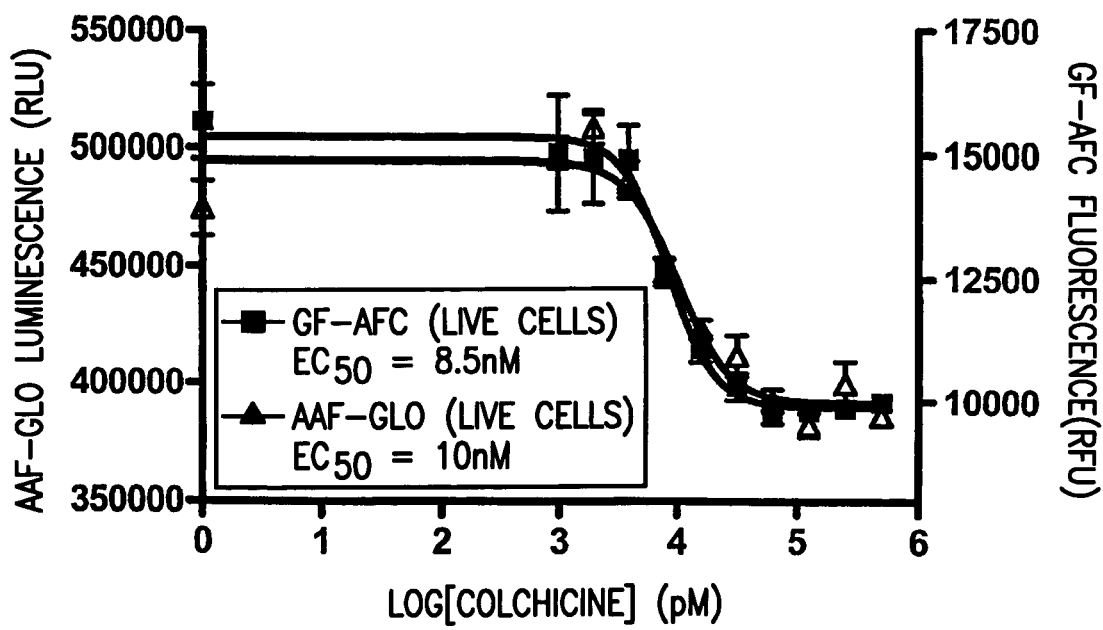

FIG. 4B shows data with colchicine (mitosis inhibitor). The highest dosage is 500 nM. The data was similar to that for GF-AFC, but it was obtained using a different "live cell" detection method and toxin.

D. Ionomycin Data

Ionomycin (a calcium ionophore which affects calcium flux across cell membranes, and therefore a model necrosis inducing agent at high concentrations) was two fold serially diluted from 100 µM in RPMI 1640+10% FBS in 50 µL volumes. Jurkat cells were added to 10,000 cells/well in a 50 µL volume. The plate was shaken briefly using an orbital shaker and then incubated for 6 hours at 37° C. CytoTox-Glo Reagent was prepared as above and added to each well in a equal volume (100 µL) per well. The plate was incubated at room temperature for 15 minutes and the dead cell signal measured using a BMG PolarStar. Digitonin (20 mg/mL in DMSO) was diluted to 300 µg/mL in CytoTox-Glo buffer and added in 20 µL volumes per well to facilitate complete cellular lysis. Luminescence was measured after 15 minutes of incubation at room temperature.

Figure 5:
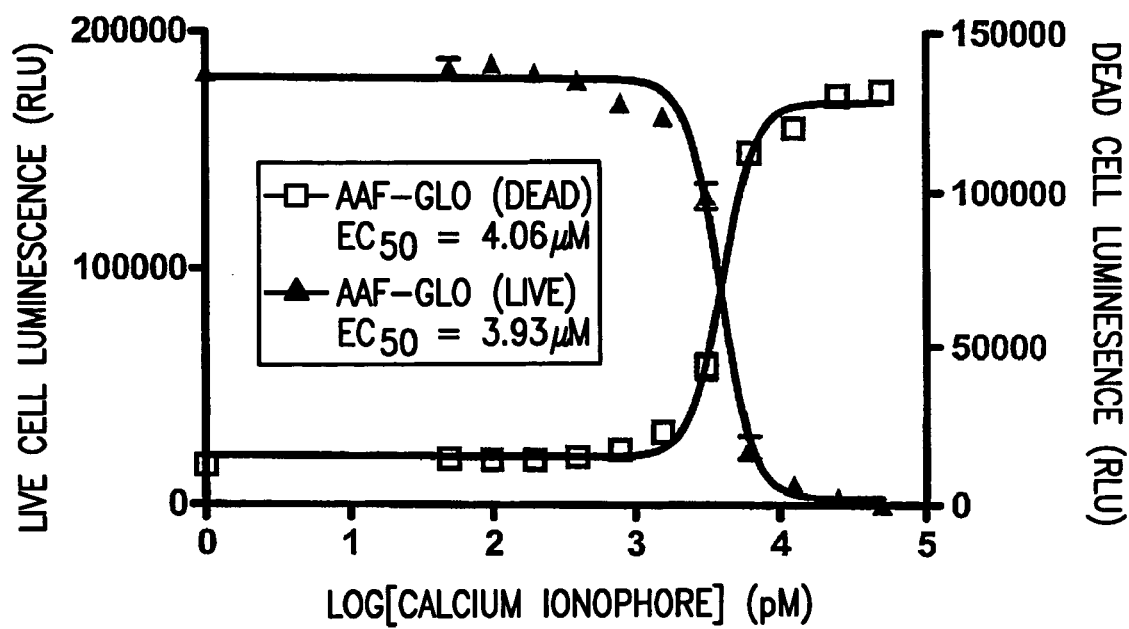
FIG. 5. Plot of log calcium ionophore versus relative live cell luminescence and relative dead cell luminescence in Jurkat cells (6 hours).

The luminescent signal collected after lysis was adjusted to reflect the "live cell" contribution by subtracting the initial dead cell signal. The data were plotted as the dead and "live cell" signals versus the concentration of ionomycin (FIG. 5). The live and dead cells were inversely complimentary using the same luminescent readout. The data also represented yet another toxin and mechanistic form of cell death.

E. Colchicine and Paclitaxel Data

HeLa cells were seeded at a density of 10,000 cells/well in DMEM+10%

Figure 6A:
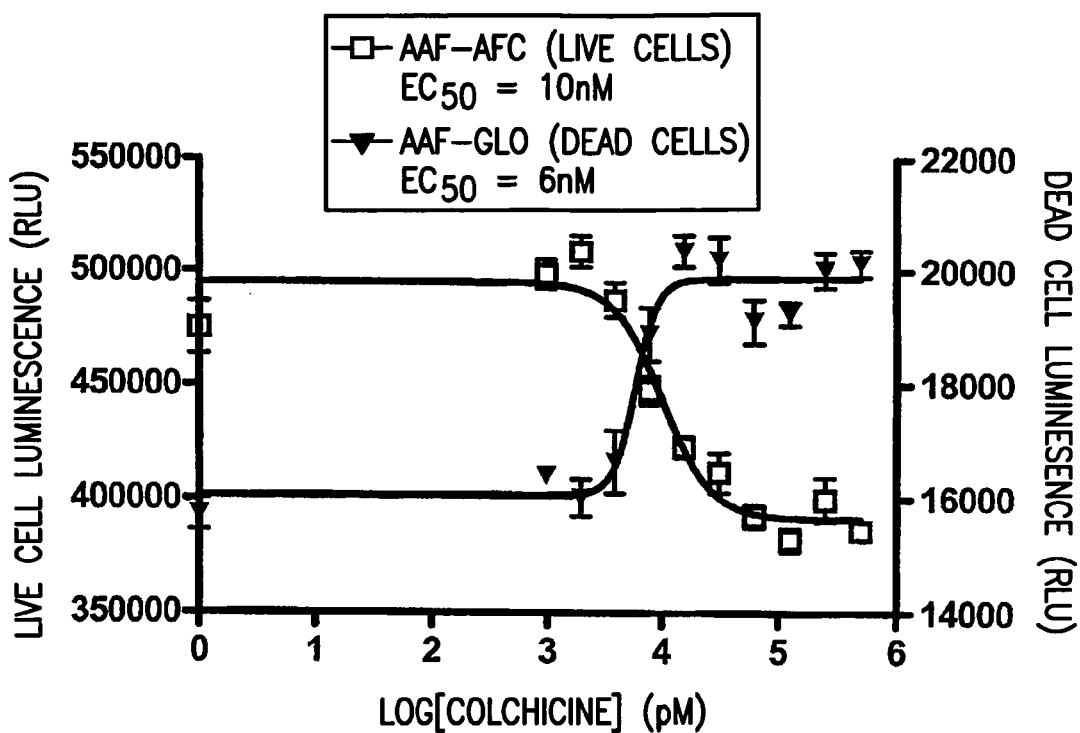
FIGS. 6A-B. A) Plot of log cochicine versus relative live cell luminescence and relative dead cell luminescence in HeLa cells (24 hours). B) Plot of log paclitaxel versus relative live cell luminescence and relative dead cell luminescence in HeLa cells (24 hours).
Figure 6B:
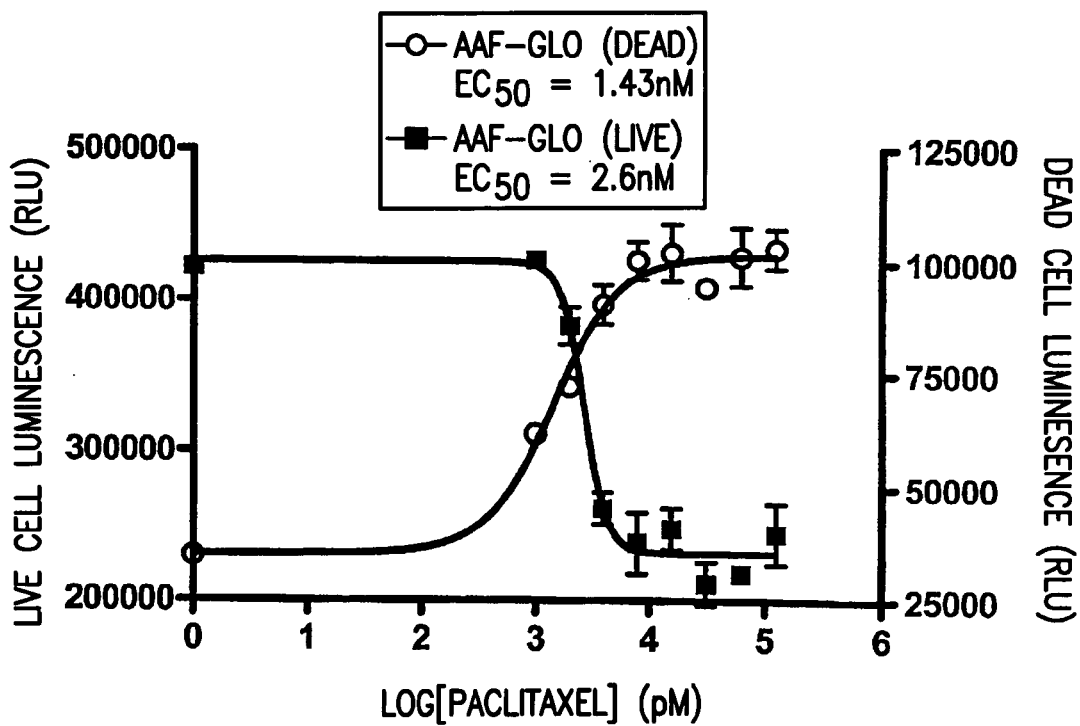

FBS in 50 µL volumes and allowed to attach overnight at 37° C. in 5% CO$_2$. Colchicine (mitosis inhibitor) was twofold serially diluted in DMEM+10% FBS in a separate plate from 1000 nM and added in 50 µL volumes (highest final dosage is 500 nM). The cells were incubated with the compound for 24 hours. CytoTox-Glo Reagent was prepared as above and added to each well in a equal volume (100 µL) per well. After 15 minutes of incubation, the dead cell signal was collected. Digitonin was added to 30 µg/mL in wells containing the AAF-Glo reagent. The plate was shaken using an orbital shaker at 700 RPM to ensure homogeneity. The resulting luminescent signal was collected using a BMG Polarstar. The dead cell signal was subtracted from the digitonin treated signal and plotted versus the dead cell signal using GraphPad Prism (FIG. 6A). The experiment was repeated using paclitaxel (FIG. 6B).

F. Staurosponin Data

Figure 7:
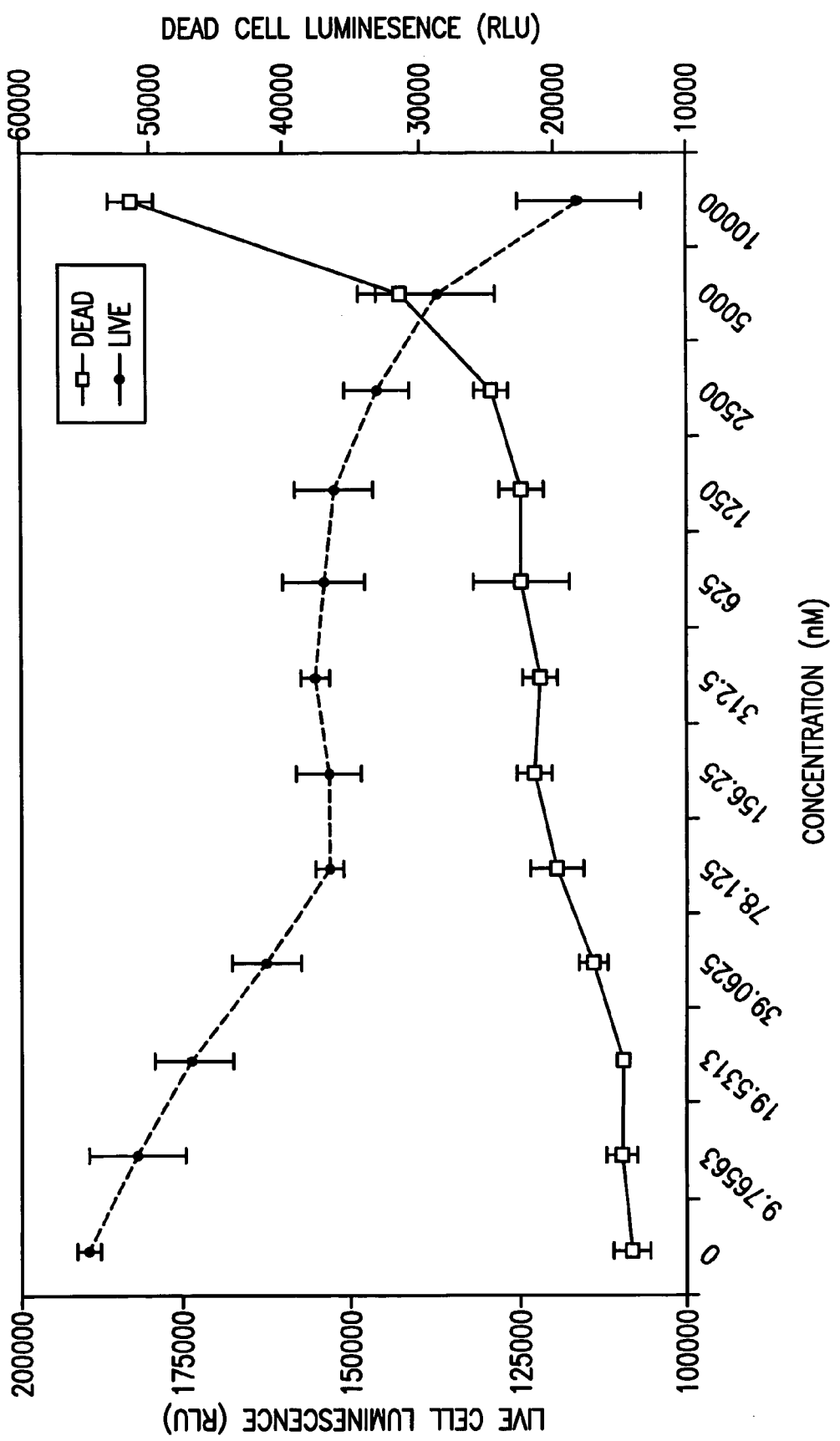
FIG. 7. Plot of staurosporine concentration versus relative live cell luminescence and relative dead cell luminescence in Jurkat cells (6 hours).

Staurosporine (multiple mechanism apoptosis inducer) was two fold serially diluted from 20 µM in RPMI 1640+10% FBS in a microwell plate in 50 µL, volumes. Jurkat cells were added to 10,000 cells/well in a 50 µL volume. The plate was shaken briefly using an orbital shaker and then incubated for 6 hours at 37° C. CytoTox-Glo Reagent was prepared as above and added to each well in a equal volume (100 µL) per well. The plate was incubated at room temperature for 15 minutes and the dead cell signal measured using a BMG PolarStar. Digitonin (20 mg/mL in DMSO) was diluted to 300 µg/mL in CytoTox-Glo buffer and added in 20 µL volumes per well to facilitate complete cellular lysis. Luminescence was measured after 15 minutes of incubation at room temperature. The luminescent signal collected after lysis was adjusted to reflect the "live cell" contribution by subtracting the initial dead cell signal (FIG. 7). The data above were plotted as the dead and "live cell" signals versus the concentration of ionomycin. The live and dead cells were inversely complimentary using the same luminescent readout. This also represents another toxin and mechanistic form of cell death.

G. Additional Jurkat Data

Figure 8:
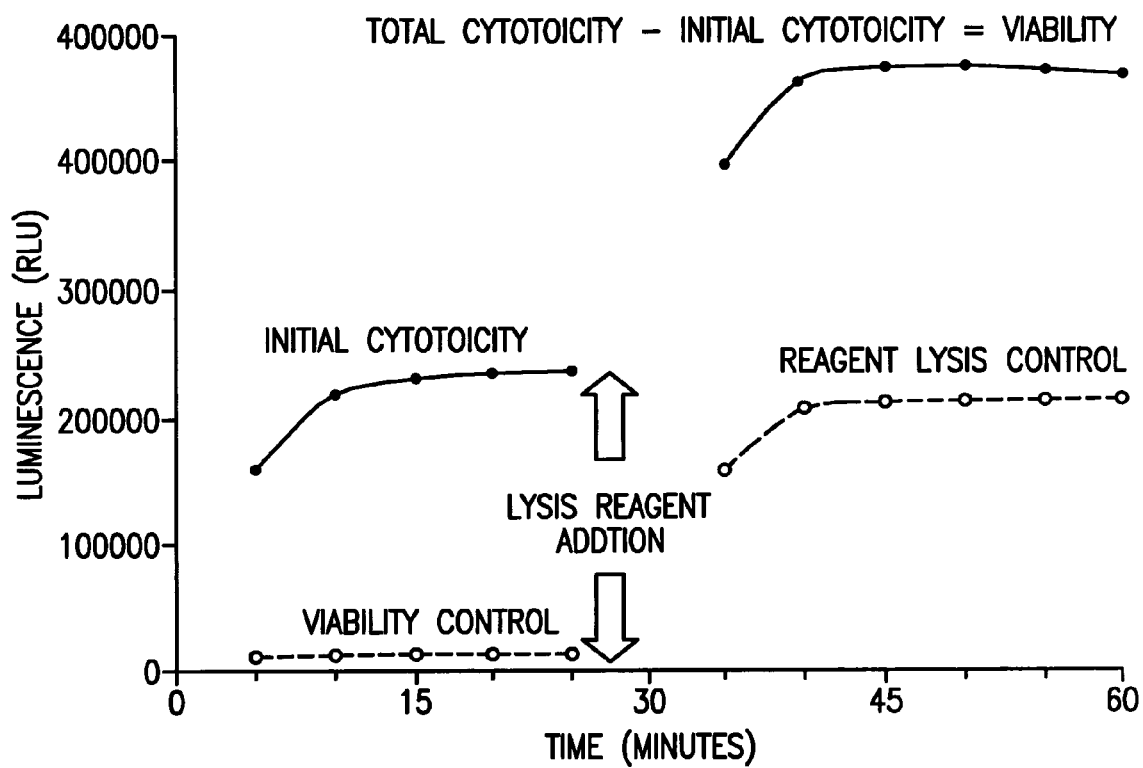
FIG. 8. Plot of time versus relative luminescence.

Jurkat cells were washed and adjusted to 50,000 cells/mL in fresh RPMI 1640+10% FBS. The pool was split: one fraction treated by mild sonication to cause cytotoxicity and the other left untreated. 50 µL of treated and 50 µL of untreated were added to the same replicate wells (100 µL final, 5000 cell/well equivalents) to represent a sample population with 50% viable and 50% cytotoxic cells. Control wells received 50 µL of untreated cells and 50 µL of RPMI 1640+10% FBS (100 µL final). AAF-aminoluciferin substrate was prepared at 200 µM in a 100 mM Hepes buffer containing 50 mM MgSO$_4$. 5.0 mL of this substrate/buffer solution was used to rehydrate a luciferin detection reagent cake. This reagent was delivered to sample and control wells at 50 µL per well. Luminescence was measured on a BMG POLARstar in kinetic mode for 25 minutes to collect the signal from the cytotoxic population. The plate was removed and digitonin added to both sample and control wells to 30 µg/mL final concentration in 15 µL volumes. After mixing by orbital shaking at 700 RPM for 1 minute, the plate was placed back in the POLARstar and luminescence from the total cytotoxicity measured in kinetic mode for an additional 25 minutes The data in FIG. 8 demonstrates that the method can be used to detect both the dead and live cell populations found in a sample using the same luminescent measure. The CytoTox-Glo Assay formulation achieves a signal steady-state (between the dead cell protease and luciferase) from 2,500 dead cells after about 10 minutes. The same number of live cells in the control well contribute a small, but measurable background signal. After addition of digitonin to lyse remaining viable cells, a new steady-state signal is reached that represents a proportional increase in the number of dead cells (5,000 total) in the sample well. Therefore, cells that were initially viable contribute to the dead cell values after lysis. Because pre- and post-lysis signals are stable after steady-state, the viable cell contribution of any sample can be determined by a subtractive method:

Viable=Total Cytotoxicity Signal−Initial Cytotoxic Signal

The "reagent lysis control" shows that digitonin-mediated cytotoxicity is equivalent to sonication in terms of lytic efficiency and does not impact the protease activity released from 2,500 viable cells.

Example II

To demonstrate the precision and accuracy of the present assay during potency testing, Jurkat cells were subjected to three different reaction conditions.

Precision

To demonstrate precision, ionomycin was two-fold serially diluted from 100 μM in RPMI 1640+10% FBS in 50 μL volumes. Duplicates of 4 wells of Jurkat cells were plated at 10,000 cells/well and incubated with diluted ionomycin for 6 hours. The CytoTox-Glo reagent was prepared as described above and added to each well in an equal volume (100 μL). The cells were incubated at room temperature for 15 minutes, and the dead cell signal was measured using a BMG Polarstar. Digitonin (20 mg/mL in DMSO) was diluted to 300 μg/mL in CytoTox-Glo buffer and added in 20 μL volumes per well to facilitate complete cellular lysis. Luminescence was measured after 15 minutes of incubation at room temperature.

Figure 9A:
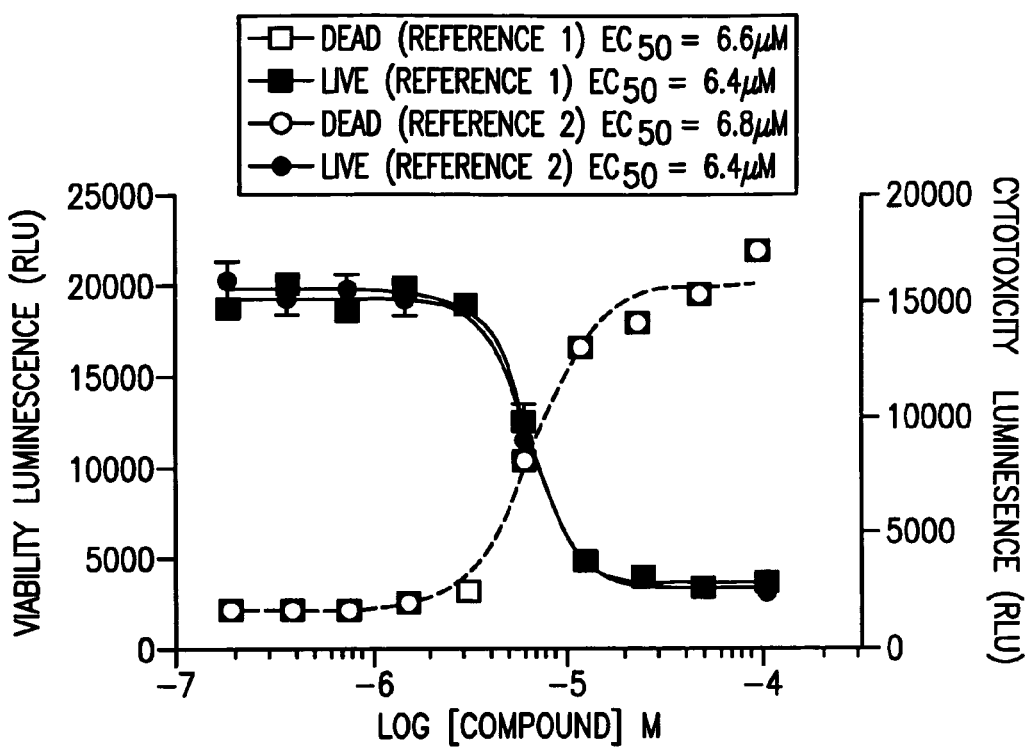
FIGS. 9A-C. A) Precision (same dose series, same number of cells, different replicate wells). Ionomycin was diluted in RPMI 1640+10% FBS, 2×4 replicates of dilution series. Jurkat cells were added and incubated for 6 hours. AAF-Glo was added, and cytotoxicity was measured after 15 minutes at room temperature (RT). Lysis reagent was added and luminescence wasmeasured again after another 15 minutes. B) Accuracy (same dose series, different numbers of cells). The same reactions as in A) except that different numbers of Jurkat cells were added to simulate errors in plating number etc. The results show the same $EC_{50}$ but a different magnitude of response due to cell number. C) Potency (different dose series, same number of cells). The same reactions as in A) except that ½ and 2× the dose of ionomycin with 10,000 cells per well was employed. This shows that the assay chemistry can detect minor differences in potency.

The luminescent signal collected after cell lysis (total luminescence possible) was adjusted to reflect the "live cell" contribution by subtracting the initial dead cell signal. The data were plotted as the dead and "live cell" signals versus the concentration of ionomycin (FIG. 9A). The $EC_{50}$ values for each duplicate were the same demonstrating the precision of the assay.

Accuracy

Figure 9B:
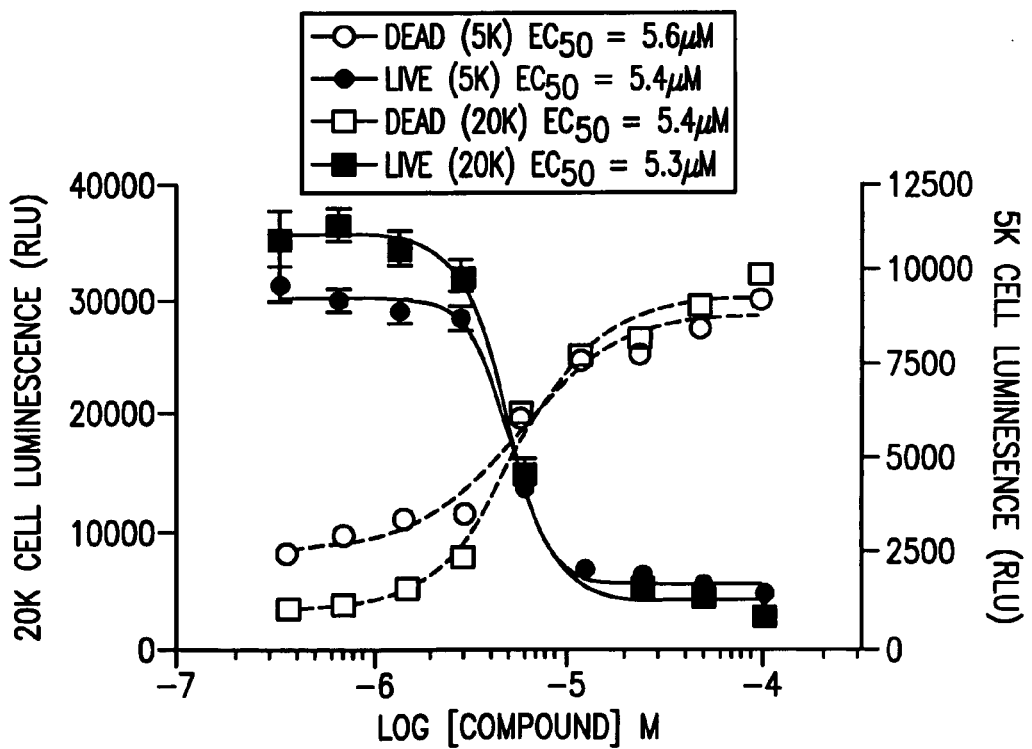

To demonstrate accuracy, reaction conditions were duplicated from above except a different number of cells (5,000 or 10,000) were used. As can be seen in FIG. 9B, the $EC_{50}$ values for each duplicate were the same despite the difference in cell number demonstrating the accuracy of assay.

Figure 9C:
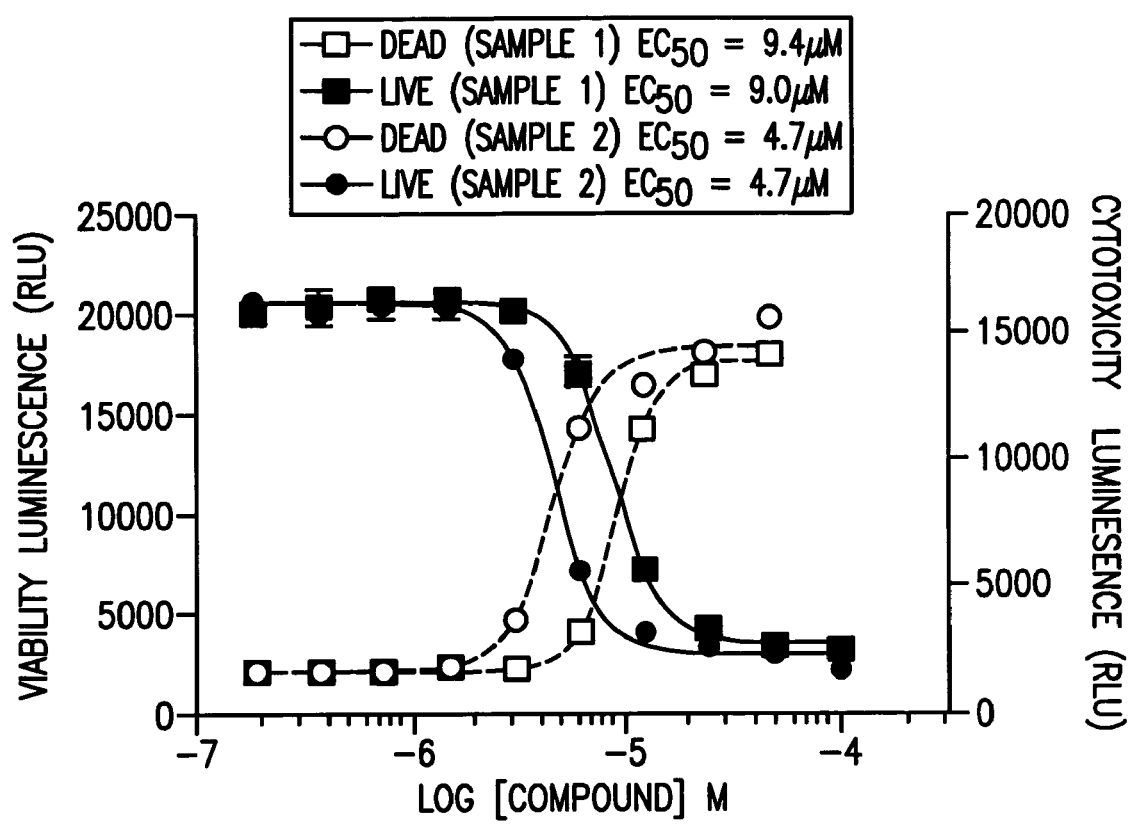

To further demonstrate accuracy as it relates to potency, reactions were performed as above except either ½ or 2× ionomycin was used. As can be seen in FIG. 9C, the $EC_{50}$ values for each duplicate were either ½ or 2× the $EC_{50}$ values obtained for the 1× concentration of ionomycin.

Example III

Epoxomicin

DU-145 cells were seeded at a density of 5,000 cells/well in 50 μL of MEM+10% FBS and allowed to attach overnight. Epoxomicin (a proteasome inhibitor) was serially diluted from 5 μM in MEM+10% FBS and added in 50 μL volumes. The cells were incubated with the compound for 48 hours. CytoTox-Glo reagent was prepared as described above and added to each well in an equal volume (100 μL). After 15 minutes of incubation, the dead cell signal was measured. Digitonin (20 mg/mL in DMSO) was diluted in CytoTox-Glo buffer and added in 20 μL volumes to each well to facilitate complete cell lysis. Luminescence was measured after 15 minutes of incubation at room temperature.

Figure 10A:
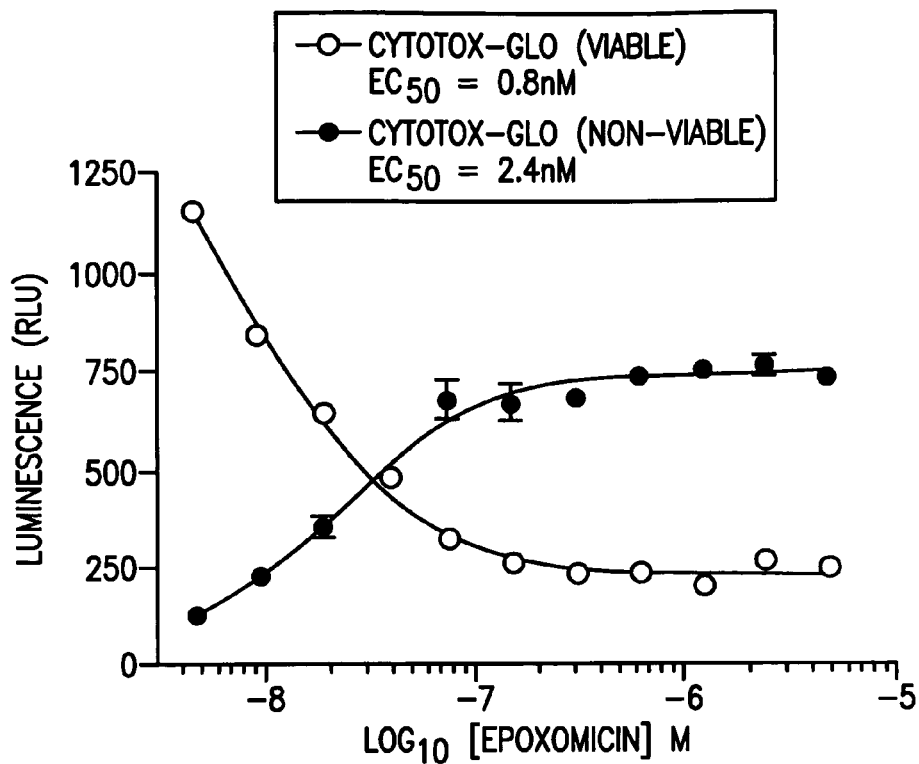
FIGS. 10 A-C. A) Dual measures of viability and cytotoxicity using the proteasome inhibitor, epoxomicin, at 48 hours. B) Two orthogonal measures of viability give comparable $EC_{50}$ to the subtractive method. C) An orthogonal measure (LDH chemistry) is comparable to luminescent dead (non-viable) cell measure.

The luminescent signal collected after lysis was adjusted to reflect the "live cell" contribution by subtracting the initial dead cell signal. The data were plotted as the non-viable and viable signals versus the concentration of epoxomicin (FIG. 10A). The viable and non-viable cells were inversely complimentary using the same luminescent readout. The data also represents yet another toxin and mechanistic form of cell death.

Orthogonal Measurements for Cell Viability

To demonstrate that values derived from the present assay are comparable to other cell viability measurements, the assay was compared to fluorescent and luminescent cell viability methods. GF-AFC was diluted to 200 μM in 100 mM HEPES, pH 7.5 and added in 100 μL volumes to epoxomicin-treated DU-145 cells. After 30 minutes of incubation at 37° C., fluorescence was measured using a BMG Polarstar. For luminescent cell viability measurement, CellTiter-Glo (Promega) was prepared by rehydrating the cake with the provided buffer and added in 100 μL volumes to parallel wells containing epoxomicin-treated DU-145 cells. The plate was shaken using an orbital shaker to ensure homogeneity. After 30 minutes of incubation at room temperature, luminescence was measured using a BMG Polarstar.

Figure 10B:
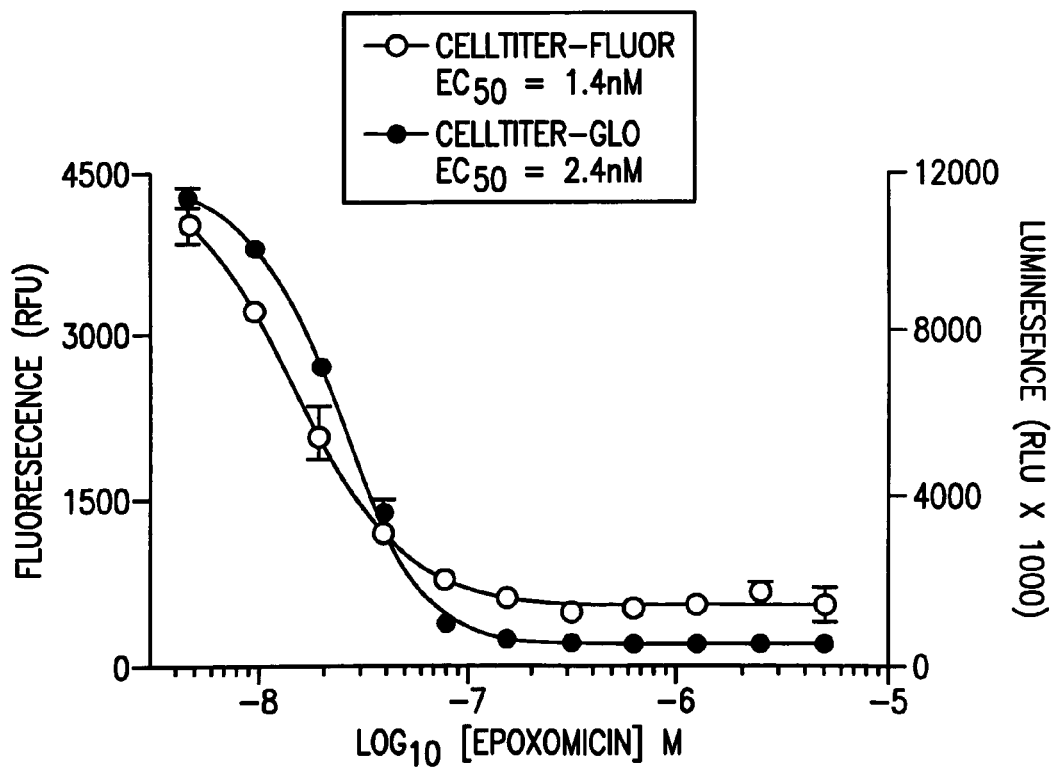

As seen in FIG. 10B, the values obtained for the fluorescent and luminescent cell viability assays are similar to the ones obtained with the present assay (FIG. 10A).

Orthogonal Measurement of Cytotoxicity

Figure 10C:
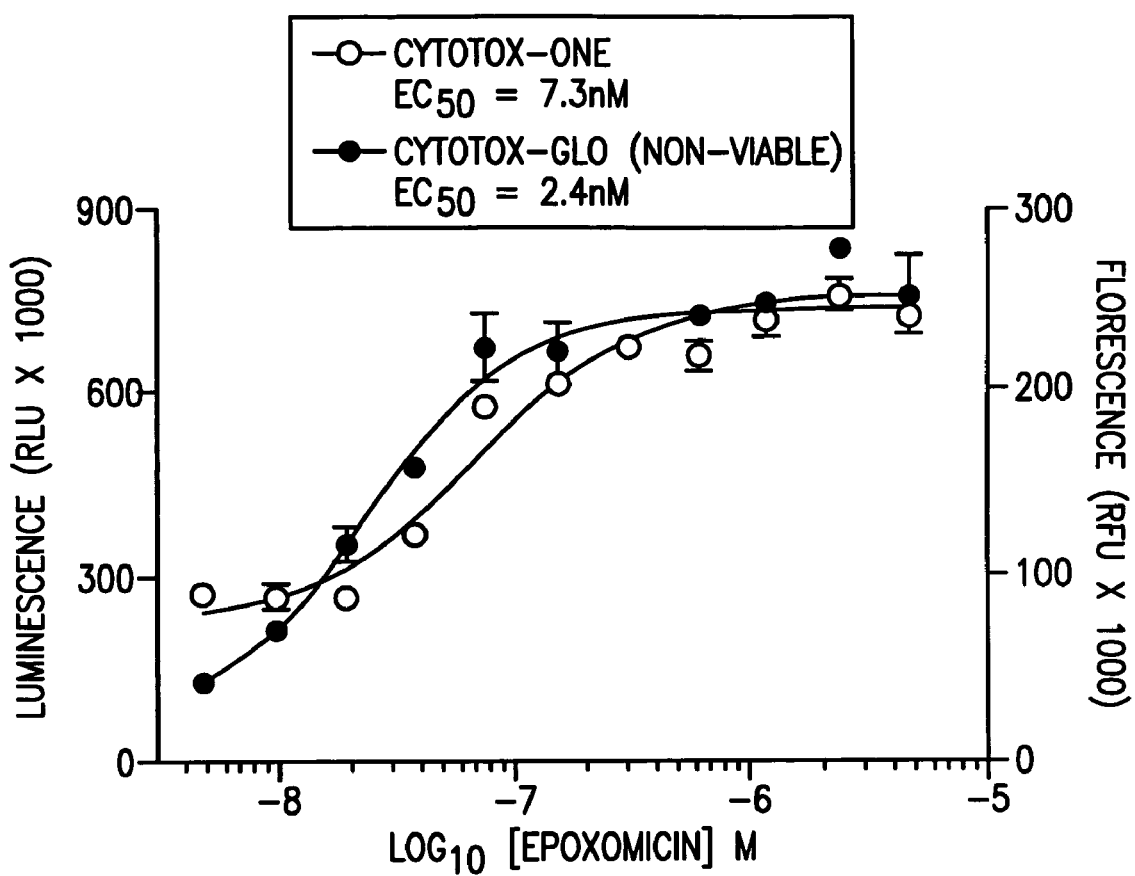

To demonstrate that cytotoxicity values derived from the present assay are comparable to other cytotoxicity measurements, the present assay was compared to a fluorescent cytotoxicity method. CytoTox-ONE™ Homogenous Membrane Integrity Assay (which measures the release of lactate dehyrogenase (LDH)) was used according to the manufacturer's (Promega) protocol. Briefly, the CytoTox-ONE™ reagent was prepared by mixing the substrate mix and assay buffer and adding 100 μL volumes to epoxomicin-treated DU-145 cells. The cells were allowed to incubate at room temperature for 10 minutes. Fluorescence was measured using a Labsystems Fluoroskan Ascent. As seen in FIG. 10C, the value obtained for the fluorescent cytotoxicity method was comparable to that obtained from the present assay.

Example IV

To demonstrate that dual measurement of cell viability and cytotoxicity mitigates false interpretations, K562cells were seeded at a density of 5,000 cells/well in RPMI 1640+10% FBS in 50 μL volumes. Campothecin was two-fold serially-diluted in RPMI 1640+10% FBS medium from 10 μM and added in 50 μL volumes. The cells were incubated at 37° C., 5% $CO_2$ for 24 hours. CytoTox-Glo reagent was prepared as described above and added to each well in an equal volume (100 μL). After 15 minutes of incubation, the dead cell signal was measured. Digitonin (20 mg/mL in DMSO) was diluted in CytoTox-Glo buffer and added in 20 μL volumes to each well to facilitate complete cell lysis. Luminescence was measured after 15 minutes of incubation at room temperature.

Figure 11A:
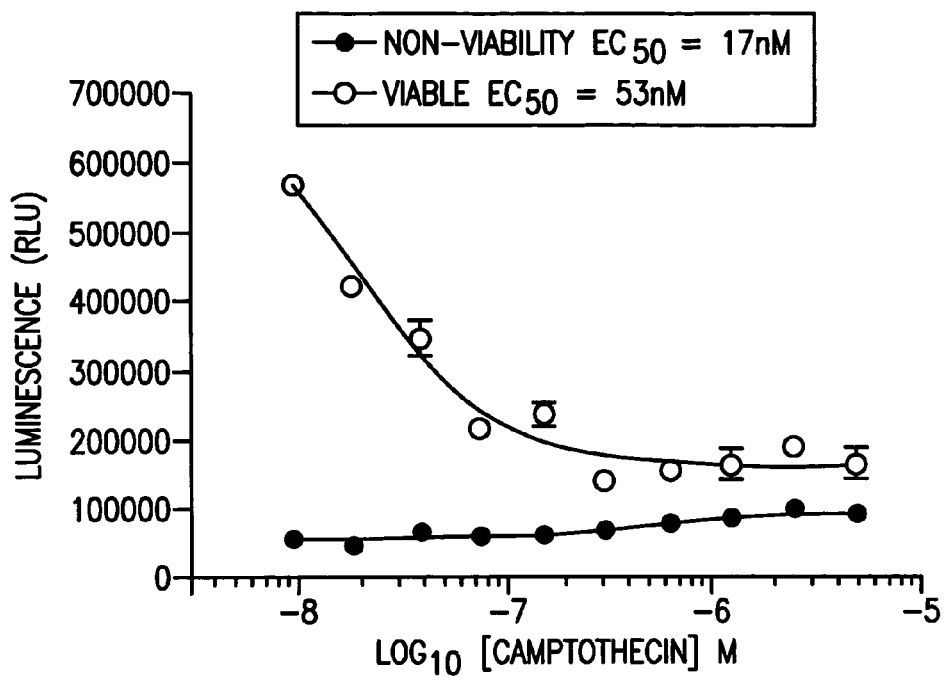
FIGS. 11A-C. A) Cell-cycle arrest with early cytotoxicity. Viable measure shows more viable cells at low doses of drug because of cell-cycle arrest at higher dosages (no division), but cytotoxicity measure shows very early cytotoxicity. B)

The luminescent signal collected after lysis was adjusted to reflect the "live cell" contribution by subtracting the initial dead cell signal. The data were plotted as the non-viable and viable signals versus the concentration of campothecin (FIG. 11A). The viability measurement shows more viable cells at low compound concentrations and fewer viable cells at higher concentrations, suggestive of cytotoxicity. However, the cytotoxicity values are not inversely correlated to viability, suggesting little or no cytotoxicity. If only viability was measured, one might conclude that the compound was substantially cytotoxic. If only cytotoxicity was measured, one might conclude that the compound was not very potent. Either interpretation would be faulty. Together, they demonstrate early cytotoxicity because of cell-cycle arrest.

Figure 11B:
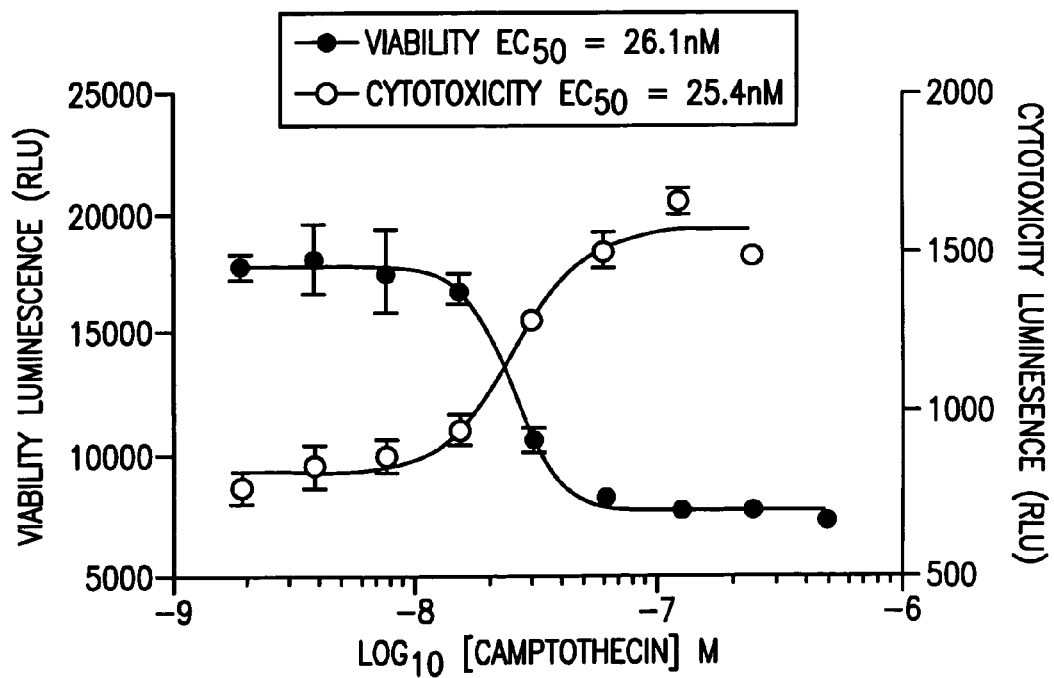

In FIG. 11B, HeLa cells were seeded at a 10,000 cells/well in DMEM+10% FBS in 50 μl volumes and incubated overnight at 37° C. in 5% $CO_2$. Nocodazole was two-fold serially diluted in DMEM+10% FBS in a separate plate from 2 μM and added in 50 μL it volumes (highest final dosage is 1,000 nM). The cells were allowed to incubate with the compound for 24 hours. CytoTox-Glo Reagent was prepared as above and added to each well in an equal volume (100 μL). After 15 minutes of incubation, the dead cell signal was collected. Digitonin (20 mg/mL in DMSO) was diluted in CytoTox-Glo buffer and added in 20 μL volumes to each well to facilitate complete cell lysis. Luminescence was measured after 15 minutes of incubation at room temperature.

The luminescent signal collected after lysis was adjusted to reflect the "live cell" contribution by subtracting the initial dead cell signal. The data were plotted as the non-viable and viable signals versus the concentration of nocodazole. The data demonstrates that viability and cytotoxicity are ratiometric because of the optimal time of measurement of cytotoxicity.

Figure 11C:
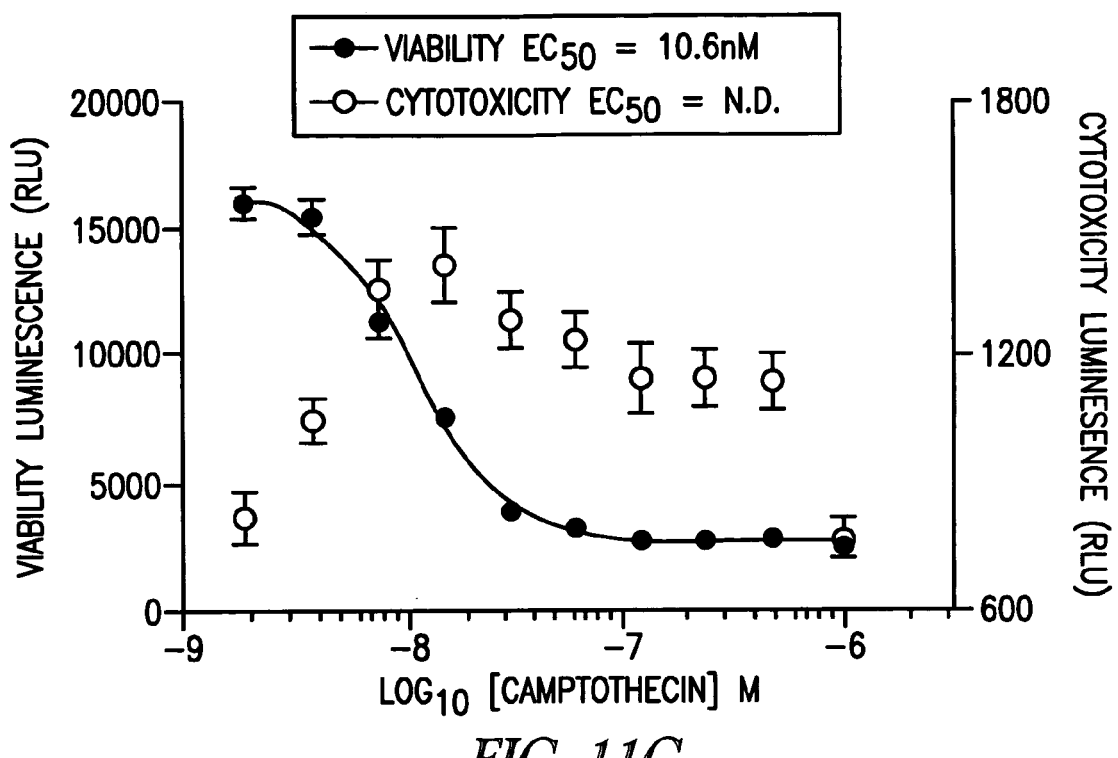

In FIG. 11C, HeLa cells were seeded at a 10,000 cells/well in DMEM+10% FBS in 50 µL volumes and incubated overnight at 37° C. in 5% $CO_2$. Colchicine was two-fold serially diluted in DMEM+10% FBS in a separate plate from 1,000 nM and added in 50 µL volumes (highest final dosage was 500 nM). The cells were allowed to incubate with the compound for 24 hours. CytoTox-Glo Reagent was prepared as above and added to each well in an equal volume (100 µL). After 15 minutes of incubation, the dead cell signal was collected. Digitonin (20 mg/mL in DMSO) was diluted in CytoTox-Glo buffer and added in 20 µL volumes to each well to facilitate complete cell lysis. Luminescence was measured after 15 minutes of incubation at room temperature.

The luminescent signal collected after lysis was adjusted to reflect the "live cell" contribution by subtracting the initial dead cell signal. The data were plotted as the non-viable and viable signals versus the concentration of colchicine. The data demonstrates that viability is reduced because of the cytotoxicity of the compound.

The decline in the strength of signal in the cytotoxicity measure reflects late stage cytotoxicity (and time-dependent cytotoxic biomarker degradation).

REFERENCES

Bond et al., *Ann. Rev. Biochem.*, 56:333 (1987).
Constam et al., *J. Biol. Chem.*, 270:26931 (1995).
Cook et al., *Anal. Biochem.*, 179:1 (1989).
Fernandes-Alnemri et al., *PNAS USA*, 93:7464 (1996).
Haunstetter et al., *Circ. Res.*, 82:1111 (1998).
Masuda-Nishimura et al., *Lett. Appl. Microbio.*, 30:130 (2000).
Miska and Geiger, *J. Clin. Chem. Clin. Biochem.*, 25:23 (1989).
Monsees et al., *Anal. Biochem.*, 221:329 (1994).
Monsees et al., *J. Biolum. Chemilum.*, 10:213 (1995).
Myers, *J. Immunol. Methods*, 212: 99 (1998).
Nicholson et al., *Nature*, 376:37 (1995).
Riss et al., *Assay and Drug Development Technologies*, 2:1 (2004).
Syntichaki et al., *Nature Reviews*, 4:672 (2003).
Tewari et al., *Cell*, 81:801 (1995).
Thornberry et al., *Nature*, 356:768 (1992).
Tran et al., *Archives of Biochemistry and Biophysics*, 403:160 (2002).
Vitnitsky et al., *J. Immunol.*, 159:554 (1997).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to detect live and dead cells in a sample, comprising:
   a) detecting luminescence in a mixture, wherein the mixture comprises a sample having cells, a bioluminogenic viable cell-impermeable substrate for a protease, and reagents for a bioluminogenic assay, and wherein the substrate is a luciferin derivative, thereby detecting the number or presence of dead cells in the sample; then
   b) lysing the cells in the mixture; and
   c) detecting luminescence in the lysed mixture, thereby detecting the number or presence of live cells in the sample.

2. A method to detect live and dead cells in a sample, comprising:
   a) detecting luminescence in a mixture, wherein the mixture comprises a sample having cells, a bioluminogenic viable cell impermeable substrate for a protease, and reagents for a bioluminogenic assay, and wherein the substrate is a luciferin derivative, thereby quantifying dead cells in the sample; then
   b) lysing the cells in the mixture; and
   c) detecting luminescence in the lysed mixture, thereby quantifying live cells in the sample.

3. The method of claim 1 wherein, prior to step (a), the sample is contacted with the substrate before the reagents.

4. The method of claim 1 wherein, prior to step (a), the sample is contacted with the reagents before the substrate.

5. The method of claim 1 wherein the sample is contacted with the reagents and the substrate at the same time prior to step (a).

6. The method of claim 1 or 2 wherein the sample is treated with a cell death inducing agent.

7. The method of claim 1 or 2 wherein the bioluminogenic viable cell impermeable substrate is a substrate for a tripeptidyl peptidase, calpain or chymotrypsin.

8. The method of claim 1 or 2 wherein the sample comprises mammalian cells.

9. The method of claim 1 or 2 wherein the substrate is Ala-Ala-Phe-aminoluciferin or Z-Leu-Leu-Val-Tyr-aminoluciferin (SEQ ID NO:13).

10. The method of claim 1 or 2 wherein the luciferin derivative is an aminoluciferin derivative.

11. The method of claim 1 or 2 wherein the substrate is a prosubstrate for a beetle luciferase.

12. The method of claim 1 or 2 further comprising detecting the presence or amount of a molecule other than the protease.

13. The method of claim 1 or 2 wherein the cells are lysed with a detergent.

14. The method of claim 1 or 2 wherein the sample is a physiological sample.

15. The method of claim 1 or 2 wherein the protease is an endoprotease.

16. The method of claim 1 or 2 wherein the protease is an exoprotease.

17. The method of claim 1 or 2 wherein the substrate for the protease is a peptide of no more than 15 residues.

18. The method of claim 2 wherein the live cells are quantified by subtracting the luminescence detected in step (a) from the luminescence detected in step (c).

19. A method to detect live and dead cells in a sample, the method comprising:
   (a) detecting luminescence in a mixture, wherein the mixture comprises a sample having cells, a bioluminogenic viable cell-impermeable substrate for a protease, and reagents for a bioluminogenic assay, and wherein the substrate is a luciferin derivative, thereby detecting the number or presence of dead cells in the sample; then
   (b) lysing the cells in the mixture; and
   (c) detecting luminescence in the lysed mixture, thereby detecting the number or presence of live cells in the sample, wherein the luminescence in step (c) results from the same bioluminogenic viable cell-impermeable substrate as the luminescence in step (a).

20. The method of claim 19, wherein the number of dead cells is detected in step (a) and the number of live cells is detected in step (c).

* * * * *

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: A synthetic peptide

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: A synthetic peptide

<400> SEQUENCE: 2

Leu Glu Thr Asp
1

<210> SEQ ID NO 3
<211> LENGTH: 4
<212> TYPE: PRT
<213> ORGANISM: Artificial Sequence
<220> FEATURE:
<223> OTHER INFORMATION: A synthetic peptide

<400> SEQUENCE: 3

Ile Glu Thr Asp
```

```
<210> SEQ ID NO 4
<211> LENGTH: 4
<212> TYPE: PRT
<213> ORGANISM: Artificial Sequence
<220> FEATURE:
<223> OTHER INFORMATION: A synthetic peptide

<400> SEQUENCE: 4

Asp Val Ala Asp
1

<210> SEQ ID NO 5
<211> LENGTH: 4
<212> TYPE: PRT
<213> ORGANISM: Artificial Sequence
<220> FEATURE:
<223> OTHER INFORMATION: A synthetic peptide

<400> SEQUENCE: 5

Leu Glu His Asp
1

<210> SEQ ID NO 6
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = W or L
<220> FEATURE:
<221> NAME/KEY: SITE
<222> LOCATION: 5
<223> OTHER INFORMATION: Xaa = any amino acid

<400> SEQUENCE: 6

Xaa Glu His Asp Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3, 5
<223> OTHER INFORMATION: Xaa = any amino acid

<400> SEQUENCE: 7

Asp Glu Xaa Asp Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa = L or V
<220> FEATURE:
<221> NAME/KEY: SITE
<222> LOCATION: 3, 5
```

```
<223> OTHER INFORMATION: Xaa = any amino acid

<400> SEQUENCE: 8

Xaa Glu Xaa Asp Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3, 5
<223> OTHER INFORMATION: Xaa = any amino acid
<220> FEATURE:
<221> NAME/KEY: SITE
<222> LOCATION: 7
<223> OTHER INFORMATION: Xaa = S or G

<400> SEQUENCE: 9

Glu Asn Xaa Tyr Xaa Gln Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 5
<223> OTHER INFORMATION: Xaa = any amino acid

<400> SEQUENCE: 10

Pro Arg Asn Lys Xaa
1               5

<210> SEQ ID NO 11
<211> LENGTH: 14
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 6
<223> OTHER INFORMATION: Xaa = K or N
<220> FEATURE:
<221> NAME/KEY: SITE
<222> LOCATION: 7
<223> OTHER INFORMATION: Xaa = M or L

<400> SEQUENCE: 11

Glu Ile Ser Glu Val Xaa Xaa Asp Ala Glu Phe Arg His Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: A synthetic peptide

<400> SEQUENCE: 12

Ser Glu Val Asn Leu Asp Ala Glu Phe Arg
1               5                   10
```

```
<210> SEQ ID NO 13
<211> LENGTH: 4
<212> TYPE: PRT
<213> ORGANISM: Artificial
<220> FEATURE:
<223> OTHER INFORMATION: A synthetic peptide

<400> SEQUENCE: 13

Leu Leu Val Tyr
1

<210> SEQ ID NO 14
<211> LENGTH: 4
<212> TYPE: PRT
<213> ORGANISM: Artificial Sequence
<220> FEATURE:
<223> OTHER INFORMATION: A synthetic peptide

<400> SEQUENCE: 14

Asp Ala Leu Lys
1

<210> SEQ ID NO 15
<211> LENGTH: 5
<212> TYPE: PRT
<213> ORGANISM: Artificial Sequence
<220> FEATURE:
<223> OTHER INFORMATION: A synthetic peptide

<400> SEQUENCE: 15

Arg Leu Arg Gly Gly
1               5

<210> SEQ ID NO 16
<211> LENGTH: 4
<212> TYPE: PRT
<213> ORGANISM: Artificial Sequence
<220> FEATURE:
<223> OTHER INFORMATION: A synthetic peptide

<400> SEQUENCE: 16

Leu Arg Gly Gly
1

<210> SEQ ID NO 17
<211> LENGTH: 8
<212> TYPE: PRT
<213> ORGANISM: Artificial Sequence
<220> FEATURE:
<223> OTHER INFORMATION: A synthetic peptide

<400> SEQUENCE: 17

Arg Pro Phe His Leu Leu Val Tyr
1               5

<210> SEQ ID NO 18
<211> LENGTH: 4
<212> TYPE: PRT
<213> ORGANISM: Artificial Sequence
<220> FEATURE:
<223> OTHER INFORMATION: A synthetic peptide

<400> SEQUENCE: 18

Glu Ala Ala Phe
1

<210> SEQ ID NO 19
<211> LENGTH: 5
```

```
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 5
<223> OTHER INFORMATION: Xaa = any amino acid

<400> SEQUENCE: 19

Ile Glu Gly Arg Xaa
1               5
```